US011186651B2

(12) United States Patent
Granade et al.

(10) Patent No.: US 11,186,651 B2
(45) Date of Patent: Nov. 30, 2021

(54) MONOCLONAL ANTIBODY FOR THE DETECTION OF THE ANTIRETROVIRAL DRUG EMTRICITABINE (FTC, 2',3'-DIDEOXY-5-FLUORO-3'-THIACYTIDINE)

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Timothy Clyde Granade, Conyers, GA (US); Ae Saekhou Youngpairoj, Snellville, GA (US); William Marshall Switzer, Decatur, GA (US); Walid M. Heneine, Atlanta, GA (US); Chou-Pong Pau, Atlanta, GA (US); HaoQiang Zheng, Johns Creek, GA (US); Jan Pohl, Tucker, GA (US)

(73) Assignee: The United States of America as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 17/255,763

(22) PCT Filed: Jul. 10, 2019

(86) PCT No.: PCT/US2019/041195
§ 371 (c)(1),
(2) Date: Dec. 23, 2020

(87) PCT Pub. No.: WO2020/014353
PCT Pub. Date: Jan. 16, 2020

(65) Prior Publication Data
US 2021/0253738 A1    Aug. 19, 2021

Related U.S. Application Data

(60) Provisional application No. 62/696,751, filed on Jul. 11, 2018.

(51) Int. Cl.
*C07K 16/44* (2006.01)
*G01N 33/577* (2006.01)

(52) U.S. Cl.
CPC .......... *C07K 16/44* (2013.01); *G01N 33/577* (2013.01); *C07K 2317/24* (2013.01); *C07K 2317/33* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 9,044,509 B2 | 6/2015 | Heneine et al. | |
| 9,579,333 B2 | 2/2017 | Heneine et al. | |
| 9,937,191 B2 | 4/2018 | Heneine et al. | |
| 10,335,423 B2 | 7/2019 | Heneine et al. | |
| 2012/0184719 A1 | 7/2012 | Sakai et al. | |
| 2017/0143745 A1 | 5/2017 | Heneine et al. | |
| 2018/0193366 A1 | 7/2018 | Heneine et al. | |
| 2019/0269708 A1 | 9/2019 | Heneine et al. | |
| 2020/0101072 A1 | 4/2020 | Garcia Lerma et al. | |
| 2020/0197419 A1 | 6/2020 | Heneine et al. | |
| 2020/0197420 A1 | 6/2020 | Heneine et al. | |
| 2020/0197421 A1 | 6/2020 | Heneine et al. | |

OTHER PUBLICATIONS

PCT International Search Report, International Application No. PCT/US2019/041195 filed Jul. 10, 2019, 5 pages (dated Nov. 25, 2019).
Gandhi, M. et al., "Development and Validation of an Immunoassay for Tenofovir in Urine as a Real-Time Metric of Antiretroviral Adherence", *EClinicalMedicine* vol. 2-3, pp. 22-28 (Aug. 2018).
Pendela, M. et al., "LC Assay for a HIV Tablet Containing Emtricitabine, Tenofovir Disoproxil Fumarate and Rilpivirine," *Chromatographia* vol. 73, No. 5-6, pp. 439-445 (Jan. 9, 2011).
Pratt, G. W. et al., "Detection of Lamivudine and Emtricitabine Using a Modified Pyrimidine Assay," 2016 IEEE Healthcare Innovation Point-of-Care Technologies Conference (HI-POCT), IEEE, pp. 78-80 (Nov. 9, 2016).

*Primary Examiner* — Nora M Rooney
(74) *Attorney, Agent, or Firm* — Klarquist Sparkman, LLP

(57) ABSTRACT

Disclosed are monoclonal antibodies that specifically bind emtricitabine (FTC). Methods are also disclosed for using these antibodies to detect FTC in samples. In some embodiments, these methods are of use for determining if a subject is complying with a therapeutic or prophylactic protocol. In other embodiments, methods are disclosed for determining the dose of FTC to administer to a subject.

38 Claims, 5 Drawing Sheets
Specification includes a Sequence Listing.

FIG. 3

Heavy chain (SEQ ID NO: 1)

```
                     10         20         30         40         50         60         70
                     ....|....|....|....|....|....|....|....|....|....|....|....|....|....|
5' RACE_VH           QVQLQQPGAELVKPGASVKVSCKASGYTFTSYWMHWVKQRPGQGLEWIGRIHLSDSDTNYNQNFKDKATL
MS/MS_VH_fully_tryptic ....................................................................
MS/MS_VH_semi_tryptic  ....................................................................

80         90        100        110        120        130        140
                     ....|....|....|....|....|....|....|....|....|....|....|....|....|....|
5' RACE_VH           TVDKSSRTAHMHLSSLTSADSAVYYCAMXXTPQSNYDTYWGQGTLVTVSA--------------------
MS/MS_VH_fully_tryptic ...........................................................AKTTPPSVYPLAPGCGDTTG
MS/MS_VH_semi_tryptic  ...........................................................AKTTPPSVYPLAPGCGDTTG 150        160        170        180        190        200        210
                     ....|....|....|....|....|....|....|....|....|....|....|....|....|....|
5' RACE_VH           ----------------------------------------------------------------------
MS/MS_VH_fully_tryptic SSVTLGCLVKGYFPESVTVTWNSGSLSSSVHTFPALLQSGLYTMSSSVTVPSSTWPSQTVTCSVAHPASS
MS/MS_VH_semi_tryptic  SSVTLGCLVKGYFPESVTVTWNSGSLSSSVHTFPALLQSGLYTMSSSVTVPSSTWPSQTVTCSVAHPASS 220        230        240        250        260        270        280
                     ....|....|....|....|....|....|....|....|....|....|....|....|....|....|
5' RACE_VH           ----------------------------------------------------------------------
MS/MS_VH_fully_tryptic TTVDKKLEPSGPISTINPCPPCKECHKCPAPNLEGGPSVFIFPPNIKDVLMISLTPKVTCVVVDVSEDDP
MS/MS_VH_semi_tryptic  TTVDKKLEPSGPISTINPCPPCKECHKCPAPNLEGGPSVFIFPPNIKDVLMISLTPKVTCVVVDVSEDDP 290        300        310        320        330        340        350
                     ....|....|....|....|....|....|....|....|....|....|....|....|....|....|
5' RACE_VH           ----------------------------------------------------------------------
MS/MS_VH_fully_tryptic DVRISWFVNNVEVHTAQTQTHREDYNSTIRVVSALPIQHQDWMSGKEFKCKVNNKDLPSPIERTISKIKG
MS/MS_VH_semi_tryptic  DVRISWFVNNVEVHTAQTQTHREDYNSTIRVVSALPIQHQDWMSGKEFKCKVNNKDLPSPIERTISKIKG 360        370        380        390        400        410        420
                     ....|....|....|....|....|....|....|....|....|....|....|....|....|....|
5' RACE_VH           ----------------------------------------------------------------------
MS/MS_VH_fully_tryptic LVRAPQVYILPPPAEQLSRKDVSLTCLVVGFNPGDISVEWTSNGHTEENYKDTAPVLDSDGSYFIYSKLD
MS/MS_VH_semi_tryptic  LVRAPQVYILPPPAEQLSRKDVSLTCLVVGFNPGDISVEWTSNGHTEENYKDTAPVLDSDGSYFIYSKLD 430        440        450
                     ....|....|....|....|....|....|
5' RACE_VH           ------------------------------
MS/MS_VH_fully_tryptic IKTSKWEKTDSFSCNVRHEGLKNYYLAKTISRSPGK
MS/MS_VH_semi_tryptic  IKTSKWEKTDSFSCNVRHEGLKNYYLAKTISRSPGK
```

Light Chain (SEQ ID NO: 2)

```
                     10         20         30         40         50         60         70
                     ....|....|....|....|....|....|....|....|....|....|....|....|....|....|
5' RACE_VL           DIQMTQSPASLSASVGETVTITCRASGNIHNYLAWYQQKQGKSPQLLVYNAKTLTDGVPSRFSGSGSGTQ
MS/MS_VL_semi_tryptic  ....................................................................
MS/MS_VL_fully_tryptic ....................................................................

80         90        100        110        120        130        140
                     ....|....|....|....|....|....|....|....|....|....|....|....|....|....|
5' RACE_VL           YSLKINSLQPEDFGNYYCQHFLTTPYTFGGGTKLEMR---------------------------------
MS/MS_VL_semi_tryptic  ..............................RADAAPTVSIFPPSSEQLTSGGASVVCFLNNFY
MS/MS_VL_fully_tryptic ..............................RADAAPTVSIFPPSSEQLTSGGASVVCFLNNFY 150        160        170        180        190        200        210
                     ....|....|....|....|....|....|....|....|....|....|....|....|....|....|
5' RACE_VL           ----------------------------------------------------------------------
MS/MS_VL_semi_tryptic  PKDINVKWKIDGSERQNGVLNSWTIQDSKDSTYSMSSTLTLTKDEYERHNSYTCEATHKTSTSPIVKSFN
MS/MS_VL_fully_tryptic PKDINVKWKIDGSERQNGVLNSWTIQDSKDSTYSMSSTLTLTKDEYERHNSYTCEATHKTSTSPIVKSFN 5' RACE_VL           ----
MS/MS_VL_semi_tryptic  RNE-
MS/MS_VL_fully_tryptic RNEC
```

MONOCLONAL ANTIBODY FOR THE DETECTION OF THE ANTIRETROVIRAL DRUG EMTRICITABINE (FTC, 2',3'-DIDEOXY-5-FLUORO-3'-THIACYTIDINE)

CROSS REFERENCE TO RELATED APPLICATIONS

This is a § 371 U.S. national stage of International Application No. PCT/US2019/041195, filed Jul. 10, 2019, which claims the benefit of U.S. Provisional Application No. 62/696,751, filed Jul. 11, 2018, which is incorporated by reference herein in its entirety.

STATEMENT OF GOVERNMENT SUPPORT

This invention was made with Government support at the Centers for Disease Control and Prevention. The United States Government has certain rights in the invention.

FIELD OF THE DISCLOSURE

This relates to monoclonal antibodies and antigen binding fragments that specifically bind to emtricitabine (FTC) and their use, for example, in methods of detecting FTC in biological samples from a subject treated with a therapeutic or prophylactic protocol that includes administration of FTC.

BACKGROUND

Significant progress has been made slowing the advancement of the symptoms of AIDS associated with HIV infection. However, in the absence of an effective vaccine, HIV continues to spread globally with an estimated 2.1 million new infections occurring in 2015. Antiretroviral therapy (ART) of HIV-infected persons resulting in durable HIV suppression has been shown to significantly reduce transmissibility of HIV. However, this approach can only provide protection for HIV-infected persons if effective concentrations of the agents are used in the infected subjects.

Daily oral pre-exposure prophylaxis (PrEP) with the combination emtricitabine (FTC) and tenofovir disoproxil fumarate (TDF) (the combination is sold as TRUVADA®) is recommended by CDC and WHO for the prevention of HIV in persons at high risk of infection. However, many people find it challenging to adhere to a daily dosing schedule and cannot fully benefit from PrEP. U.S. Pat. No. 9,044,509 was issued to the CDC in 2015 for a method of protecting a primate host against HIV infection by administering FTC in combination with tenofovir or TDF. The effectiveness of PrEP depends on the level of adherence to daily dosing. Monitoring of drug adherence can improve drug compliance to PrEP and maximize PrEP effectiveness. In a recent study, a 50% increase in adherence was observed among PrEP participants identified as non-compliant by drug monitoring (Landovitz JAIDS 2017). Available assays for drug monitoring rely on complex analytical methods such as mass spectrometry-based tests that are specialized, centralized, costly, and mostly not available for routine clinical testing. A need remains to develop simple, scalable, and inexpensive assays to detect FTC for adherence monitoring in persons receiving PrEP or ART. It would be advantageous to develop a simple immunodiagnostic kit that can be used in a clinical lab or at the point-of-care to detect FTC and provide information to assist with patient retention and adherence.

SUMMARY OF THE DISCLOSURE

Disclosed herein are isolated monoclonal antibodies and antigen binding fragment thereof that include a heavy chain variable domain and a light chain variable domain, wherein the heavy chain variable domain includes a heavy chain complementarity determining region (HCDR)1, an HCDR2 and an HCDR3, and wherein the light chain variable domain includes a light chain complementarity determining region (LCDR)1, an LCDR2 and an LCDR3, and wherein the antibody specifically binds FTC. In some embodiments, the heavy chain variable domain includes the HCDR1, HCDR2 and HCDR3 of SEQ ID NO: 1 as determined using a method of Paratome, Kabat, Chothia or IMGT, and wherein the light chain variable domain includes the LCDR1, LCDR2 and LCDR3 of SEQ ID NO: 2, as determined using the method of Paratome, Kabat, Chothia or IMGT, and wherein the HCDR1, HCDR2, HCDR3, HCDR3, LCDR1, LCDR2 and LCDR3 are determined using the same method.

Methods of using these antibodies are also disclosed herein, such as for the detection of FTC in biological samples. In some embodiments, these methods can be used to determine if a subject is complying with a therapeutic, PrEP, or PEP protocol that includes the use of FTC. In other embodiments, methods are disclosed for determining the dose of FTC to administer to a subject.

The foregoing and other features and advantages of the invention will become more apparent from the following detailed description of several embodiments which proceeds with reference to the accompanying figures.

BRIEF DESCRIPTION OF THE FIGURES

FIG. 3. Comparison of MS/MS and 5' RACE amino acid sequences—an alignment of the sequences showed 100% identity of the overlapping MS/MS and 5'RACE regions (represented by dots in the alignment). SEQ ID NO: 1 AND SEQ ID NO: 2 are shown.

SEQUENCE LISTING

Figure 1:
FIG. 1. Basic structural chemistry of FTC attached to a heptanoic spacer and a six amino acid peptide. The peptide was conjugated to Limulus polyphemus hemocyanin (LPH), dextran (a branched glucan), or bovine serum albumin (BSA) via the available sulfhydryl group of the cysteine to proteins that serve as the FTC immunogen (LPH) and as the material to identify FTC antibodies (BSA or dextran).

The nucleic and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [4239-

100766-06_Sequence_Listing.txt, Dec. 23, 2020, 10.0 K], which is incorporated by reference herein. In the accompanying sequence listing:

SEQ ID NO: 1 is the amino acid sequence of the heavy chain variable domain of the 5D2 monoclonal antibody.

```
QVQLQQPGAE LVKPGASVKV SCKASGYTFT SYWMHWVKQR

PGQGLEWIGR IHLSDSDTNY NQNFKDKATL TVDKSSRTAH

MHLSSLTSAD SAVYYCAMGG TFQSNYDTYW GQGTLVTVSA

AKTTPPSVYP LAPGCGDTTG SSVTLGCLVK GYFPESVTVT

WNSGSLSSSV HTFPALLQSG LYTMSSSVTV PSSTWPSQTV

TCSVAHPASS TTVDKKLEPS GPISTINPCP PCKECHKCPA

PNLEGGPSVF IFPPNIKDVL MISLTPKVTC VVVDVSEDDP

DVRISWFVNN VEVHTAQTQT HREDYNSTIR VVSALPIQHQ

DWMSGKEFKC KVNNKDLPSP IERTISKIKG LVRAPQVYIL

PPPAEQLSRK DVSLTCLVVG FNPGDISVEW TSNGHTEENY

KDTAPVLDSD GSYFIYSKLD IKTSKWEKTD SFSCNVRHEG

LKNYYLKKTI SRSPGK
```

SEQ ID NO: 2 is the amino acid sequence of the light chain variable domain of the 5D2 monoclonal antibody.

```
DIQMTQSPAS LSASVGETVT ITCRASGNIH NYLAWYQQKQ

GKSPQLLVYN AKTLTDGVPS RFSGSGSGTQ YSLKINSLQP

EDFGNYYCQH FLYTPYTFGG GTKLEMRRAD AAPTVSIFPP

SSEQLTSGGA SVVCFLNNFY PKDINVKWKI DGSERQNGVL

NSWTDQDSKD STYSMSSTLT LTKDEYERHN SYTCEATHKT

STSPIVKSFN RNEC
```

SEQ ID NO: 3 is a nucleic acid sequence encoding the heavy chain variable domain of the 5D2 monoclonal antibody.

```
GGGCTTCAGTGAAGGTGTCCTGCAAGGCATCTGGCTACACCTTCACCAG

CTACTGGATGCACTGGGTGAAGCAGAGGCCTGGCCAAGGCCTTGAGTGG

ATTGGAAGGATTCATCTTTCTGATAGTGATACTAACTACAATCAAAACT

TCAAGGACAAGGCCACATTGACTGTAGACAAATCCTCCCGCACAGCCCA

CATGCATCTCAGCAGCCTGACATCTGCGGACTCTGCGGTCTATTATTGT

GCAATGGGGGGACCTTCCAGAGTAACTACGATACTTACTGGGGCCAAG

GGACTCTGGTCACTGTCTCTGCA
```

SEQ ID NO: 4 is a nucleic acid sequence encoding the light chain variable domain of the 5D2 monoclonal antibody.

```
ATGAGTGTGCTCACTCAGGTCCTGGCGTTGCTGCTGCTGTGGCTTACAG

GTGCCAGATGTGACATCCAGATGACTCAGTCTCCAGCCTCCCTATCTGC

ATCTGTGGGAGAAACTGTCACCATCACATGTCGAGCAAGTGGGAATATT

CACAATTATTTAGCATGGTATCAGCAGAAACAGGGAAAATCTCCTCAGC

TCCTGGTCTATAATGCAAAAACCTTAACAGATGGTGTGCCATCAAGGTT

CAGTGGCAGTGGATCAGGAACACAATATTCTCTCAAGATCAACAGCCTG

CAGCCTGAAGATTTTGGGAATTATTACTGTCAACATTTTTTGTATACTC

CTTACACGTTCGGAGGGGGGACCAAGCTGGAAATGAGA
```

SEQ ID NO: 5 is an amino acid sequence of a leader.
MRWSCLILFLLATTPGVHS
SEQ ID NO: 6 is a VDJ recombination amino acid sequence.

```
QVQLQQPGAELVKPGASVKVSCKASGYTFTSYWMHWVKQRPGQGLEWIG

RIHLSDSDTNYNQNFKDKATLTVDKSSRTAHMHLSSLTSADSAVYYCAM

GGTFQSNYDTYWGQGTLVTVSA
```

SEQ ID NO: 7 is an amino acid sequence of a leader.
MSVLTQVLALLLLWLTGARC (SEQ ID NO: 7)
SEQ ID NO: 8 is a VJ recombination amino acid sequence.

```
DIQMTQSPASLSASVGETVTITCRASGNIHNYLAWYQQKQGKSPQLLVY

NAKTLTDGVPSRFSGSGSGTQYSLKINSLQPEDFGNYYCQHFLYTPYTF

GGGTKLEMR
```

DETAILED DESCRIPTION OF SEVERAL EMBODIMENTS

Disclosed herein are isolated monoclonal antibodies and antigen binding fragment thereof that include a heavy chain variable domain and a light chain variable domain, wherein the heavy chain variable domain includes a heavy chain complementarity determining region (HCDR)1, an HCDR2 and an HCDR3, and wherein the light chain variable domain includes a light chain complementarity determining region (LCDR)1, an LCDR2 and an LCDR3, and wherein the antibody specifically binds FTC. These antibodies are of use to detect FTC in samples, such as biological samples.

In some embodiments, the heavy chain variable domain includes the HCDR1, HCDR2 and HCDR3 of SEQ ID NO: 1 as determined using a method of Paratome, Kabat, Chothia or IMGT, and wherein the light chain variable domain includes the LCDR1, LCDR2 and LCDR3 of SEQ ID NO: 2, as determined using the method of Paratome, Kabat, Chothia or IMGT, and wherein the HCDR1, HCDR2, HCDR3, HCDR3, LCDR1, LCDR2 and LCDR3 are determined using the same method. Nucleic acid molecules encoding these heavy and light chain variable domains, expression vectors including these nucleic acids molecules, and host cells including these expression vectors are also disclosed.

Methods of using these antibodies are also disclosed herein, such as for the detection of FTC in biological samples, for determining if a subject is complying with a therapeutic or prophylactic protocol including FTC, or for determining if a therapeutic or prophylactic protocol is effective for treating or preventing an HIV infection in a subject.

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. To facilitate review of the various embodiments, the following explanations of terms are provided:

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes. An anti-retroviral agent can be administered by any route, including oral administration.

Agent: Any substance or any combination of substances that is useful for achieving an end or result; for example, a substance or combination of substances useful for inhibiting or preventing an immunodeficiency virus, such as an HIV, infection in a subject. Agents include proteins, nucleic acid molecules, compounds, small molecules, organic compounds, inorganic compounds, or other molecules of interest. An agent can include a therapeutic/prophylactic agent (such as an anti-retroviral agent), a diagnostic agent or a pharmaceutical agent.

Anti-retroviral agent: An agent that specifically inhibits a retrovirus from replicating or infecting cells. Non-limiting examples of antiretroviral drugs include entry inhibitors (e.g., enfuvirtide), CCRS receptor antagonists (e.g., vicriviroc, maraviroc), reverse transcriptase inhibitors (e.g., lamivudine, zidovudine, abacavir, tenofovir and prodrugs thereof, emtricitabine, efavirenz), protease inhibitors (e.g., lopinavir, ritonavir, darunavir, atazanavir), integrase inhibitors (raltegravir, dolutegravir, elvitegravir, bictegravir), maturation inhibitors (e.g., bevirimat and vivecon).

Anti-retroviral therapy (ART): A therapeutic treatment for HIV-1 infection involving administration of at least one anti-retroviral agents (e.g., one, two, three or four anti-retroviral agents) to an HIV-1 infected individual. One example of an ART protocol includes treatment with a combination of FTC and another agent. The agent can be tenofovir or a tenofovir prodrug (for example, tenofovir disproxil fumarate and tenofovir alfenamide). In some examples, ART includes Highly Active Anti-Retroviral Therapy (HAART). One example of a HAART protocol includes treatment with a combination of FTC, tenofovir disproxil fumarate (TDF) or tenofovir alfenamide (TAF), elvitagravir (EVG), and cobicistat (COBI).

Antibody: An immunoglobulin, antigen-binding fragment, or derivative thereof, that specifically binds and recognizes an analyte (antigen) such as FTC. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used in the methods disclosed herein.

In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, $3^{rd}$ Ed., W.H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a bispecific or bifunctional antibody has two different binding sites.

Typically, a naturally occurring immunoglobulin has heavy chains and light chains interconnected by disulfide bonds Immunoglobulin genes include the kappa, lambda, alpha, gamma, delta, epsilon and mu constant region genes, as well as the myriad immunoglobulin variable domain genes. There are two types of light chains, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (see, e.g., Kindt et al. Kuby Immunology, 6th ed., W.H. Freeman and Co., page 91 (2007).) References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab. In several embodiments, the $V_H$ and $V_L$ combine to specifically bind the antigen. In additional embodiments, only the $V_H$ is required. For example, naturally occurring camelid antibodies consisting of a heavy chain only are functional and stable in the absence of light chain (see, e.g., Hamers-Casterman et al., *Nature,* 363:446-448, 1993; Sheriff et al., *Nat. Struct. Biol.,* 3:733-736, 1996). Any of the disclosed antibodies includes a heterologous constant region. For example the antibody includes a constant region that is different from a native constant region, such as a constant region including one or more modifications (such as the "LS" mutations) to increase half-life.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). Paratome (see Kunik, PLoS Comput Biol 8(2): e1002388. doi:10.1371/journal.pcbi.1002388, and Kunik et al., Nucleic Acids Res. 2012 July; 40(Web Server issue): W521-4. doi: 10.1093/nar/gks480. Epub 2012 Jun. 6, program available on the internet at ofranservices.biu.ac.il/index.html) identifies antigen binding regions (ABRs) that are like CDRs in that these six regions (three in the heavy chain, three in the light chain) are responsible for antigen binding. The Paratome ABRs and IMGT, Kabat and Clothia CDRs partially overlap, and all contain antigen binding residues within a given antibody. Thus, when used herein, the term "CDR" include CDRs identified by any method, such as Kabat, IMGT or Clothia, and as used herein also includes the Paratome ABRs. The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are referred to as LCDR1, LCDR2, and LCDR3. Heavy chain CDRs are referred to as HCDR1, HCDR2, and HCDR3. A reference to a HCDR or a LCDR includes the Paratome ABRs.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples, monoclonal antibodies are isolated from a subject. Monoclonal antibodies can have conservative amino acid substitutions, which have substantially no effect on antigen binding or other immunoglobulin functions. (See, for example, Harlow & Lane, *Antibodies, A Laboratory Manual,* $2^{nd}$ ed. Cold Spring Harbor Publications, New York (2013).) In some embodiments, any of the antibodies disclosed herein can be a monoclonal antibody.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, and are typically of different species. In some examples, a chimeric antibody includes one or more CDRs and/or framework regions from one human antibody and CDRs and/or framework regions from another human antibody.

A "fully human antibody" or "human antibody" is an antibody, which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel.* 1st Ed. New York: Cold Spring Harbor Laboratory Press, 2004. Print.; Lonberg, *Nat. Biotech.,* 23: 1117-1125, 2005; Lonenberg, *Curr. Opin. Immunol.,* 20:450-459, 2008)

Biological sample: A sample obtained from a subject. Biological samples include all clinical samples useful for detection of disease or infection (for example, HIV-1 infection) in subjects, and useful for assessing concentration of anti-retroviral agents, including, but not limited to, cells, tissues, and bodily fluids, such as blood, derivatives and fractions of blood (such as serum), urine, cerebrospinal fluid; as well as biopsied or surgically removed tissue, for example tissues that are unfixed, frozen, or fixed in formalin or paraffin. Additional biological samples include hair and nails. In one example, a biological sample is obtained from a subject having or suspected of having an HIV-1 infection. In another example, a biological sample is obtained from a subject that is therapeutically or prophylactically treated with at least one anti-retroviral agent.

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, *Antibodies, A Laboratory Manual,* 2nd ed. Cold Spring Harbor Publications, New York (2013), for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography Immunological binding properties of selected antibodies may be quantified using methods well known in the art.

Conjugate: A complex of two molecules linked together, for example, linked together by a covalent bond. In one embodiment, an antibody is linked to an effector molecule, such as an antibody that specifically binds to FTC covalently linked to a detectable label. In another embodiment, the conjugate is FTC linked to a carrier protein. The linkage can be by chemical or recombinant means. In one embodiment, the linkage is chemical, wherein a reaction between the antibody moiety and the detectable label has produced a covalent bond formed between the two molecules to form one molecule. A peptide linker (short peptide sequence) can optionally be included between the antibody and the effector molecule, such as the detectable label, or FTC and the carrier molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially affect or decrease a function of a protein, such as the ability of the protein to interact with a target protein. For example, an FTC-specific antibody includes up to 1, 2, 3, 4, 5, 6, 7, 8, 9, or up to 10 conservative substitutions compared to a reference antibody sequence and retain specific binding activity for FTC. The term conservative variation also includes the use of a substituted amino acid in place of an unsubstituted parent amino acid.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the FTC-specific antibody, such as the ability to specifically bind to FTC. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example a chemical antigen that contacts another polypeptide, such as an antibody.

Control: A reference standard. In some embodiments, the control is a negative control, such a subject not treated with FTC. In other embodiments, the control is a positive control, such as a sample obtained from a subject treated with a therapeutic or prophylactic protocol including FTC, wherein the subject is compliant with the treatment or prophylactic protocol. In still other embodiments, the control is a historical control or standard reference value or range of values (such as a previously tested control sample, such as a group of subjects known to be compliant with a therapeutic or prophylactic protocol that includes FTC, a group of samples that represent normal values, or a sample matrix that includes (such as spiked with) a known concentration of FTC).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Degenerate variant: In the context of the present disclosure, a "degenerate variant" refers to a polynucleotide encoding a protein (for example, an antibody that specifically binds FTC or variable region thereof) that includes a sequence that is degenerate as a result of the genetic code. There are twenty natural amino acids, most of which are specified by more than one codon. Therefore, all degenerate nucleotide sequences are included as long as the amino acid sequence of the antibody that binds FTC encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include avidin, biotin, fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached with spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, 4th ed, Cold Spring Harbor, N.Y., 2012) and Ausubel et al. (In Current Protocols in Molecular Biology, John Wiley & Sons, New York, through supplement 104, 2013).

Detecting: To identify the existence, presence, or fact of something, such as the amount of FTC in a sample. General methods of detecting are known to the skilled artisan and may be supplemented with the protocols and reagents disclosed herein.

Effective amount: The amount of an agent (such as an anti-retroviral agent) that alone, or together with one or more additional agents, induces the desired response, such as an inhibition of an HIV infection or prevention of an HIV infection.

Effector molecule: A molecule intended to have or produce a desired effect; for example, a desired effect on a cell to which the effector molecule is targeted. Effector molecules include, for example, polypeptides and small molecules. In one non-limiting example, the effector molecule is a detectable label. The skilled artisan will understand that some effector molecules may have or produce more than one desired effect.

Emtricitabine: 2'-deoxy-5-fluoro-3'thiacytidine (FTC). FTC is sold under the trade name EMTRIVA® (emtricitabine) formerly COVIRACIL®), is a nucleoside reverse transcriptase inhibitor (NRTI) used in the treatment of HIV infection in adults and children, and to prevent an HIV infection. Emtricitabine is also marketed in a fixed-dose combination with tenofovir disproxil fumarate (Viread) under the brand name TRUVADA® for therapeutic and prophylactic uses (for treating or preventing an HIV infection). A fixed-dose triple combination of emtricitabine, tenofovir and efavirenz (Sustiva, marketed by Bristol-Myers Squibb) was approved by the U.S. Food and Drug Administration (FDA) on Jul. 12, 2006 under the name ATRIPLA®. Emtricitabine also makes up one fourth of the four drug ("Quad") combination known as STRIBILD®.

Epitope: An antigenic determinant. These are particular chemical groups or peptide sequences on a molecule that are antigenic, i.e. that elicit a specific immune response. An antibody specifically binds a particular antigenic epitope. In some examples a disclosed antibody specifically binds to an epitope on FTC.

Expression: Transcription or translation of a nucleic acid sequence. For example, an encoding nucleic acid sequence (such as a gene) can be expressed when its DNA is transcribed into an RNA or RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression includes controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc region: The polypeptide including the constant region of an antibody excluding the first constant immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region includes immunoglobulin domains Cγ2 and Cγ3 and the lower part of the hinge between Cγ1 and Cγ2. Although the boundaries of the Fc region may vary, the human IgG heavy chain Fc region is usually defined to include residues C226 or P230 to its carboxyl-terminus, wherein the numbering is according to the EU index as in Kabat. For IgA, the Fc region includes immunoglobulin domains Cα2 and Cα3 and the lower part of the hinge between Cα1 and Cα2. Any of the disclosed antibodies includes a heterologous Fc region or heterologous constant domain. For example the antibody includes a Fc region or constant domain that is different from a native Fc region or constant domain, such as a Fc region or constant domain including one or more modifications (such as the "LS" mutations) to increase half-life.

Human Immunodeficiency Virus (HIV): A retrovirus that causes immunosuppression in humans (HIV disease), and leads to a disease complex known as the acquired immunodeficiency syndrome (AIDS). There are two general types of HIV, called HIV type 1 (HIV-1) and HIV-2. "HIV-1 disease" refers to a well-recognized constellation of signs and symptoms (including the development of opportunistic infections) in persons who are infected by an HIV-1 virus, as determined by serologic or molecular studies. Laboratory findings associated with this disease include a progressive decline in T cells. Related viruses that are used as animal models include simian immunodeficiency virus (SIV) and feline immunodeficiency virus (FIV). Treatment of HIV with HAART has been effective in reducing the viral burden and ameliorating the effects of HIV-1 infection in infected individuals and also for interrupting transmission. There are also specific prophylactic protocols, such as but not limited to the use of TRUVADA®, that can be used prophylactically to reduce the risk of acquiring HIV infection.

IgA: A polypeptide belonging to the class of antibodies that are substantially encoded by a recognized immunoglobulin alpha gene. In humans, this class or isotype includes $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class includes $IgG_1$, $IgG_2$, $IgG_3$, and $IgG_4$. In mice, this class includes $IgG_1$, $IgG_{2a}$, $IgG_{2b}$, $IgG_3$.

Immune complex: The binding of antibody or antigen binding fragment (such as a scFv) to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography Immunological binding properties of selected antibodies may be quantified using methods well known in the art.

Inhibiting or treating a disease: Inhibiting the full development of a disease or condition, for example, in a subject who is at risk for a disease such as acquired immunodeficiency syndrome (AIDS). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" method is a treatment administered to a subject who does not exhibit signs of a disease, such as an infection, or a method that prevents an infection, such as with HIV.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Lateral flow device: Devices that include bibulous or non-bibulous matrices capable of transporting analytes and reagents to a pre-selected site. Many such devices are commercially available, in which the strips are made of nitrocellulose, paper, cellulose, and other bibulous materials. Non-bibulous materials can be used and rendered bibulous by applying a surfactant to the material.

Lateral flow strip: A test strip used in lateral flow chromatography, in which a test sample fluid, suspected of containing an analyte, flows (for example by capillary action) through the strip (which is frequently made of materials such as paper or nitrocellulose). The test fluid and any suspended analyte can flow along the strip to a detection zone in which the analyte (if present) interacts with a detection agent to indicate a presence, absence and/or quantity of the analyte.

Linker: A bi-functional molecule that can be used to link two molecules into one contiguous molecule, for example, to link an effector molecule to an antibody. In some embodiments, the provided conjugates include a linker between the effector molecule or detectable marker and an antibody. In some cases, a linker is a peptide within an antigen binding fragment (such as an Fv fragment) which serves to indirectly bond the $V_H$ and $V_L$. Non-limiting examples of peptide linkers include a $(G_4S)_1$ linker, a $(G_4S)_2$ linker, or a $(G_4S)_3$ linker.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Nucleoside analog reverse-transcriptase inhibitors (NRTIs): The initial class of antiretroviral drugs that was developed. In order to be incorporated into the viral nucleic acids, NRTIs must be activated in the cell by the addition of phosphate groups to their deoxyribose moiety, to form NRTI triphosphates. This phosphorylation step is carried out by cellular kinase enzymes. NRTIs include zidovudine, didanosine, zalcitabine, stavudine, lamivudine, abacavir, and emtricitabine (also called FTC).

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Science,* 22th ed., Pharmaceutical Press, London, UK (2012), describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers comprises, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as on-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms comprises one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Polypeptide modifications: polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full-length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Specifically bind: When referring to an antibody or antigen binding fragment, refers to a binding reaction which determines the presence of a target protein, peptide, or polysaccharide in the presence of a heterogeneous population of proteins and other biologics. Thus, under designated conditions, an antibody binds preferentially to a particular target (such as FTC) and does not bind in a significant amount to other chemicals, proteins or nucleotides present in the sample or subject. Specific binding can be determined by methods known in the art. With reference to an antibody-antigen complex, specific binding of the antigen and antibody can refer to a $K_D$ of less than about $10^{-7}$ Molar, such as less than about $10^{-8}$ Molar, $10^{-9}$, or even less than about $10^{-19}$ Molar.

$K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

The antibodies disclosed herein specifically bind to a defined target (or multiple targets, in the case of a bispecific antibody). Thus, an antibody that specifically binds to FTC is an antibody that binds substantially to FTC, including a solid substrate to which the FTC is attached, or FTC in a biological specimen. It is, of course, recognized that a certain degree of non-specific interaction may occur between an antibody or conjugate including an antibody (such as an antibody that specifically binds FTC or conjugate including such antibody) and a non-target (such as a biological sample that does not include FTC or a different substrate). Typically, specific binding results in a much stronger association between the antibody and FTC than between the antibody and a sample lacking FTC. Specific binding typically results in greater than 2-fold, such as greater than 5-fold, greater than 10-fold, or greater than 100-fold increase in amount of bound antibody (per unit time) to a FTC, solid substrate including (for example, covalently bound to) FTC, or a biological sample including the FTC, as compared to a sample or solid substrate lacking the FTC epitope. Specific binding under such conditions requires an antibody that is selected for its specificity for a particular epitope. A variety of immunoassay formats are appropriate for selecting antibodies or other ligands specifically immunoreactive with a particular epitope, such as on FTC. For example, solid-phase ELISA immunoassays are routinely used to select monoclonal antibodies specifically immunoreactive with a molecule. See Harlow & Lane, *Antibodies, A Laboratory Manual*, $2^{nd}$ ed., Cold Spring Harbor Publications, New York (2013), for a description of immunoassay formats and conditions that can be used to determine specific immunoreactivity.

Subject: Living multi-cellular vertebrate organisms, a category that includes human and non-human mammals. In an example, a subject is a human. In a particular example, the subject is a newborn infant. In an additional example, a subject is selected who is in need of inhibiting of an HIV-1 infection. For example, the subject is either uninfected and at risk of HIV-1 infection or is infected in need of treatment.

Therapeutic agent: Used in a generic sense, it includes treating agents, prophylactic agents, and replacement agents. A therapeutic agent is used to ameliorate a specific set of conditions in a subject with a disease or a disorder, such as an HIV infection.

Therapeutically effective amount and prophylactically effective amount: A quantity of a specific substance, such as a disclosed agent, sufficient to achieve a desired effect in a subject being treated. A therapeutically effective amount can be the amount necessary to inhibit an immunodeficiency virus replication, treat AIDS in a subject with an existing infection with the immunodeficiency virus. "Prophylactically effective amounts" refers to administration of an agent (or combination) that inhibits or prevents establishment of a self-replicating infection with an infectious agent, such as an immunodeficiency virus, for example HIV. Post-exposure prophylaxis (PEP) is the prevention or inhibition of an immunodeficiency virus infection, wherein the active agent (s) are administered after a potential exposure to an immunodeficiency virus such as HIV. The exposure can be recreational (sexual, drug related, etc.) or occupational (such as from a needle stick or contaminated blood product in the hospital setting). Pre-exposure prophylaxis (PrEP) is the prevention or inhibition of an immunodeficiency virus infection in a host, wherein the active agent(s) are administered prior to any possible infection (e.g., prior to any exposure) of the subject with the virus. "Protection" as used in the context of a host primate response to an immunodeficiency virus challenge is defined by the host primate being serologically negative and negative in a polymerase chain reaction (PCR) testing for viral genome.

Transformed: A transformed cell is a cell into which a nucleic acid molecule has been introduced by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Treating or preventing a disease: Preventing a disease refers to inhibiting the full development of a disease or condition, for example, in a subject who is at risk of or has an HIV-1 infection. Treating a disease refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease for the purpose of reducing the risk of developing pathology.

The term "prevents" does not necessarily mean that an agent completely eliminates the disease or condition, so long as at least one characteristic of the disease or condition is eliminated. Thus, an agent that inhibits or prevents an infection, can, but does not necessarily completely eliminate such an infection, so long as the infection is measurably diminished, for example, by at least about 50%, such as by at least about 70%, or about 80%, or even by about 90% the infection in the absence of the agent, or in comparison to a reference agent.

Unit dosage form: A physically discrete unit, such as a capsule, tablet, or solution, that is suitable as a unitary dosage for a human patient, each unit containing a predetermined quantity of one or more active ingredient(s) calculated to produce a therapeutic effect, in association with at least one pharmaceutically acceptable diluent or carrier, or combination thereof. Unit dosage formulations contain a daily dose or an appropriate fraction thereof, of the active ingredient(s). FTC can be administered alone or in combination with other agents in unit dosage forms.

Vector: A vector comprises nucleic acid sequences (for example, mRNA or DNA) that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. In some embodiments, a viral vector is provided that comprises one or more nucleic acid molecules encoding a heavy or light chain variable region of a disclosed antibody or antigen binding fragment that specifically binds to FTC, or an scFv fragment. In some embodiments, the viral vector can be an adeno-associated virus (AAV) vector. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV).

Suitable methods and materials for the practice or testing of this disclosure are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and supplements to 2012); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual,* Cold Spring Harbor Laboratory Press, 1990; and Harlow and Lane, *Using Antibodies: A Laboratory Manual,* Cold Spring Harbor Laboratory Press, 1999. In case of conflict, the present specification, including explanations of terms, will control.

II. Description of Several Embodiments

Isolated monoclonal antibodies that specifically bind FTC are disclosed herein. Antigen binding fragments of such antibodies, conjugates thereof, and methods of using these molecules, are provided herein. The antibodies can be chimeric or humanized. Also disclosed herein are compositions including these monoclonal antibodies and a pharmaceutically acceptable carrier. Nucleic acids encoding these antibodies, expression vectors comprising these nucleic acids, and isolated host cells that express the nucleic acids are also provided. These antibodies have a high sensitivity and specificity, and can be used to detect FTC in biological samples A. Monoclonal Antibodies and Antigen Binding Fragments Isolated monoclonal antibodies are disclosed herein that specifically bind to FTC. In several embodiments, the monoclonal antibodies include a heavy chain comprising a heavy chain complementarity determining region (HCDR)1, a HCDR2 and an HCDR3, and a light chain comprising a light chain complementarity determining region (LCDR) 1, LCDR2 and LCDR3. The disclosed antibodies specifically bind to FTC. In some embodiments, the FTC specific antibodies include a variable heavy ($V_H$) and a variable light ($V_L$) chain and specifically bind FTC. In several embodiments, the antibody or antigen binding fragment thereof includes heavy and light chain variable regions including the HCDR1, HCDR2, and HCDR3 of the amino acid sequence set forth as SEQ ID NO: 1 and LCDR1, LCDR2, and LCDR3 of the amino acid sequence set forth as SEQ ID NO: 2, see the list of sequences above.

The discussion of monoclonal antibodies below refers to isolated monoclonal antibodies that include heavy and light chain variable domains including at least one complementarity determining region (CDR), such as a CDR1, CDR2 and CDR3. The person of ordinary skill in the art will understand that various CDR numbering schemes (such as the Paratome, Kabat, Chothia or IMGT numbering schemes) can be used to determine CDR positions. The person of skill in the art will readily understand use of various CDR numbering schemes when referencing particular amino acids of the antibodies disclosed herein.

In some embodiments, disclosed is an isolated monoclonal antibody or antigen binding fragment thereof that specifically binds FTC, wherein the monoclonal antibody includes a heavy chain variable domain and a light chain variable domain, wherein the heavy chain variable domain includes a HCDR1, an HCDR2 and an HCDR3, and wherein and wherein the light chain variable domain includes a LCDR1, an LCDR2 and an LCDR3. The heavy chain variable domain includes the HCDR1, HCDR2 and HCDR3 of SEQ ID NO: 1 as determined using a method of Paratome, Kabat, Chothia or IMGT, and wherein the light chain variable domain includes the LCDR1, LCDR2 and LCDR3 of SEQ ID NO: 2, as determined using the method of Paratome, Kabat, Chothia or IMGT, and wherein the HCDR1, HCDR2, HCDR3, HCDR3, LCDR1, LCDR2 and LCDR3 are determined using the same method. It should be noted that the CDRs can be identified using other methods known to those of skill in the art, for example, Contact and Enhanced Clothia (also called Clothia+).

In some embodiments, the HCDR1 includes the amino acid sequence set forth as amino acids 27 to 35 of SEQ ID NO: 1, the HCDR2 includes the amino acid sequence set forth as amino acids 47 to 60 of SEQ ID NO: 1, and the HCDR3 includes the amino acid sequence set forth as amino acids 98 to 109 of SEQ ID NO: 1, and wherein the LCDR1 includes the amino acid sequence set forth as amino acids 27 to 34 of SEQ ID NO: 2, the LCDR2 includes the amino acid sequence set forth as amino acids 46 to 56 of SEQ ID NO:2, and the LCDR3 includes the amino acid sequence set forth as amino acids 89 to 96 of SEQ ID NO: 2.

In other embodiments, the HCDR1 includes the amino acid sequence set forth as amino acids 31 to 36 of SEQ ID NO: 1, the HCDR2 includes the amino acid sequence set forth as amino acids 50 to 66 of SEQ ID NO: 1, and the HCDR3 includes the amino acid sequence set forth as amino acids 99 to 109 of SEQ ID NO: 1, and wherein the LCDR1 includes the amino acid sequence set forth as amino acids 24 to 34 of SEQ ID NO: 2, the LCDR2 includes the amino acid sequence set forth as amino acids 50 to 56 of SEQ ID NO:2, and the LCDR3 includes the amino acid sequence set forth as amino acids 89 to 97 of SEQ ID NO: 2.

In further embodiments, the HCDR1 includes the amino acid sequence set forth as amino acids 26 to 32 of SEQ ID NO: 1, the HCDR2 includes the amino acid sequence set forth as amino acids 51 to 58 of SEQ ID NO: 1, and the HCDR3 includes the amino acid sequence set forth as amino acids 97 to 109 of SEQ ID NO: 1, and wherein the LCDR1 includes the amino acid sequence set forth as amino acids 27 to 32 of SEQ ID NO: 2, the LCDR2 includes the amino acid sequence set forth as amino acids 50 to 52 of SEQ ID NO:2, and the LCDR3 includes the amino acid sequence set forth as amino acids 89 to 96 of SEQ ID NO: 2.

In additional embodiments, the monoclonal antibody includes the HCDRs encoded by SEQ ID NO: 3 or a degenerate variant thereof and the LCDRs encoded by SEQ ID NO: 4 or a degenerate variant thereof. In more embodiments, the HCDR1 is encoded by nucleic acids 91 to 105 of SEQ ID NO: 3 or a degenerate variant thereof, the HCDR2 is encoded by nucleic acids 148 to 198 of SEQ ID NO: 3 or a degenerate variant thereof, and the HCDR3 is encoded by nucleic acids 295 to 327 of SEQ ID NO: 3 or a degenerate variant thereof, and wherein the LCDR1 is encoded by nucleic acids 70 to 102 of SEQ ID NO: 4 or a degenerate variant thereof, the LCDR2 is encoded by nucleic acids 148 to 168 of SEQ ID NO:4 or a degenerate variant thereof, and the LCDR3 is encoded by nucleic acids 265 to 285 of SEQ ID NO: 4 or a degenerate variant thereof. In further embodiments, the HCDR1 is encoded by nucleic acids 76 to 99 of SEQ ID NO: 3 or a degenerate variant thereof, the HCDR2 is encoded by nucleic acids 151 to 174 of SEQ ID NO: 3 or a degenerate variant thereof, and the HCDR3 is encoded by nucleic acids 289 to 293 of SEQ ID NO: 3 or a degenerate variant thereof, and wherein the LCDR1 is encoded by nucleic acids 79 to 96 of SEQ ID NO: 4 or a degenerate variant thereof, the LCDR2 is encoded by nucleic acids 148 to 156 of SEQ ID NO:4 or a degenerate variant thereof, and the LCDR3 is encoded by nucleic acids 265 to 285 of SEQ ID NO: 4 or a degenerate variant thereof. In some embodiments, the monoclonal antibody includes the HCDRs encoded by SEQ ID NO: 3 and the LCDRs encoded by SEQ ID NO: 4

In some embodiments, the antibody includes a heavy chain variable region including an amino acid sequence at least 95%, 96%, 97%, 98%, or 99% identical to the amino acid sequence of SEQ ID NO: 1. In more embodiments, the antibody includes a light chain variable region including an amino acid sequence at least 95%, 96%, 97%, 98%, or 99% identical to the amino acid sequence of SEQ ID NO: 2. In additional embodiments, the antibody includes both a heavy chain variable region including an amino acid sequence at least 95%, 96%, 97%, 98%, or 99% identical to the amino acid sequence of SEQ ID NO: 1, and a light chain variable region including an amino acid sequence at least 95%, 96%, 97%, 98%, or 99% identical to the amino acid sequence of SEQ ID NO: 2. In yet other embodiments, the antibody includes a heavy chain variable region encoded by a nucleic acid sequence at least 95%, 96%, 97%, 98%, or 99% identical to the nucleic acid sequence of SEQ ID NO: 3 or a degenerate variant thereof. In further embodiments, the antibody includes a light chain variable region encoded by a nucleic acid sequence at least 95%, 96%, 97%, 98%, or 99% identical to the nucleic acid sequence of SEQ ID NO: 4 or a degenerate variant thereof. In yet other embodiments, the antibody includes a heavy chain variable region encoded by a nucleic acid sequence at least 95%, 96%, 97%, 98%, or 99% identical to the nucleic acid sequence of SEQ ID NO: 3 and a light chain variable region encoded by a nucleic acid sequence at least 95%, 96%, 97%, 98%, or 99% identical to the nucleic acid sequence of SEQ ID NO: 4. In some examples, these antibodies can include the HCDRs and LCDRS as identified by IMGT, Kabbat, Chothia, or Paratome.

In additional embodiments, the antibody includes a heavy chain variable region including, or consisting of, the amino acid sequence set forth as SEQ ID NO: 1. In more embodiments, the antibody includes a light chain variable region including, or consisting of, the amino acid sequence set forth as SEQ ID NO: 2. In yet other embodiment, the antibody includes both a heavy chain variable domain including, or consisting of, the amino acid sequence set forth as SEQ ID NO: 1 and a light chain variable domain including, or consisting of, the amino acid sequence set forth as SEQ ID NO: 2.

In several embodiments, the disclosed antibodies can specifically bind FTC with an affinity, for example, of at least about $1.0 \times 10^{-8}$ M, at least about $5.0 \times 10^{-8}$ M, at least about $1.0 \times 10^{-9}$ M, at least about $5.0 \times 10^{-9}$ M, at least about $1.0 \times 10^{-10}$ M, at least about $5.0 \times 10^{-10}$ M, or at least about $1.0 \times 10^{-11}$ M.

The monoclonal antibodies can be mouse monoclonal antibodies. Chimeric antibodies are also provided. The antibodies can include any suitable framework region, such as (but not limited to) a human, monkey, rat, goat, sheep, or a rabbit framework region. Human framework regions, and mutations that can be made in a human antibody framework regions, are known in the art (see, for example, in U.S. Pat. No. 5,585,089, which is incorporated herein by reference). Alternatively, a heterologous framework region, such as, but not limited to a different mouse framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993).

In some embodiments, an antibody that specifically binds FTC as disclosed herein includes up to 10 amino acid substitutions (such as up to 1, 2, 3, 4, 5, 6, 7, 8, or up to 9 amino acid substitutions) in the framework regions of the heavy chain of the antibody, the light chain of the antibody, or the both heavy and light chains of the antibody. In some embodiments, these substitutions do not alter the binding affinity for FTC, as determined by statistical assays known in the art.

In certain embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody includes an Fc region, the carbohydrate attached thereto may be altered. Native antibodies produced by mammalian cells typically include a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In several embodiments, the constant region of the antibody includes one or more amino acid substitutions to optimize in vivo half-life of the antibody. The serum half-life of IgG Abs is regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al., *J Immunol.*, 176:346-356, 2006); M428L and N434S (the "LS" mutation, see, e.g., Zalevsky, et al., *Nature Biotechnology*, 28:157-159, 2010); N434A (see, e.g., Petkova et al., *Int. Immunol.*, 18:1759-1769, 2006); T307A, E380A, and N434A (see, e.g., Petkova et al., *Int. Immunol.*, 18:1759-1769, 2006); and M252Y, S254T, and T256E (see, e.g., Dall'Acqua et al., *J. Biol. Chem.*, 281:23514-23524, 2006). The disclosed antibodies and antigen binding fragments can be linked to a Fc polypeptide including any of the substitutions listed above, for example, the Fc polypeptide includes the M428L and N434S substitutions.

The antibody or antigen binding fragment can be derivatized or linked to another molecule (such as another peptide, protein, or a label). In general, the antibody or antigen binding fragment is derivatized such that the binding to FTC is not affected adversely by the derivatization or labeling. For example, the antibody or antigen binding fragment can be functionally linked (by chemical coupling, genetic fusion, noncovalent association or otherwise) to one or more other molecular entities, such as a detectable marker or a protein or peptide that can mediate association of the antibody or antibody portion with another molecule (such as a streptavidin core region or a polyhistidine tag). Antibody conjugates are disclosed below.

Antigen binding fragments are encompassed by the present disclosure, such as Fab, F(ab')$_2$, and Fv which include a heavy chain and $V_L$ and specifically bind F. In several embodiments, the antigen binding fragment includes the heavy and light chain variable regions from the 5D2 antibody, or any antibody disclosed herein.

These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the $V_L$ and $V_L$ expressed as two chains; and (5) Single chain antibody (such as scFv), defined as a genetically engineered molecule containing the $V_H$ and the $V_L$ linked by a suitable polypeptide linker as a genetically fused single chain molecule (see, e.g., Ahmad et al., *Clin. Dev. Immunol.*, 2012, doi:10.1155/2012/980250; Marbry, IDrugs, 13:543-549, 2010). The intramolecular orientation of the $V_H$-domain and the $V_L$-domain in a scFv, is not decisive for the provided antibodies (e.g., for the provided multispecific antibodies). Thus, scFvs with both possible arrangements ($V_H$-domain-linker domain-$V_L$-domain; $V_L$-domain-linker domain-$V_H$-domain) may be used.

(6) A dimer of a single chain antibody (scFV$_2$), defined as a dimer of a scFV. This has also been termed a "minianti-body."

Methods of making these fragments are known in the art (see for example, Harlow and Lane, *Antibodies: A Laboratory Manual*, 2$^{nd}$, Cold Spring Harbor Laboratory, New York, 2013).

In some embodiments, the antigen binding fragment can be an Fv antibody, which is typically about 25 kDa and contain a complete antigen-binding site with three CDRs per each heavy chain and each light chain. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the $V_H$ and the $V_L$ are chemically linked by disulfide bonds. In an additional example, the Fv fragments include $V_H$ and $V_L$ chains connected by a peptide linker. These single-chain antigen binding proteins (scFv) can be prepared by constructing a nucleic acid molecule encoding the $V_H$ and $V_L$ domains connected by an oligonucleotide. The nucleic acid molecule is inserted into an expression vector, which is subsequently introduced into a host cell such as a mammalian cell. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; Ahmad et al., *Clin. Dev. Immunol.*, 2012, doi:10.1155/2012/980250; Marbry, *IDrugs*, 13:543-549, 2010). Dimers of a single chain antibody (scFV$_2$), are also contemplated.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Antigen binding single $V_H$ domains, called domain antibodies (dAb), have also been identified from a library of murine $V_H$ genes amplified from genomic DNA of immunized mice (Ward et al. *Nature* 341:544-546, 1989). Human single immunoglobulin variable domain polypeptides capable of binding antigen with high affinity have also been described (see, for example, PCT Publication Nos. WO 2005/035572 and WO 2003/002609). The CDRs disclosed herein can also be included in a dAb. Bispecific forms of the disclosed antibodies and antigen binding fragments can also be produced.

B. Conjugates

The antibodies and antigen binding fragments that specifically bind to an epitope on FTC can be conjugated to an agent, such as an effector molecule, for example a detectable marker, using any number of means known to those of skill in the art. Both covalent and noncovalent attachment means may be used. One of skill in the art will appreciate that various effector molecules and detectable markers can be used, including (but not limited to) toxins and radioactive agents, and other labels, target moieties and ligands, etc. The choice of a particular effector molecule or detectable marker depends on the particular target molecule or cell, and the desired biological effect.

A monoclonal antibody that specifically binds FTC (or antigen binding fragment thereof) can be conjugated with a detectable marker; for example, a detectable marker capable of detection by ELISA, spectrophotometry, flow cytometry, microscopy or diagnostic imaging techniques. The detectable marker may be synthetic markers that are non-naturally occurring. Specific, non-limiting examples of detectable markers include avidin/biotin, fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. An antibody or antigen binding fragment may be conjugated to gold. It should be noted that the avidin itself can be conjugated with an enzyme or a fluorescent label.

An antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

An antibody or antigen binding fragment can be conjugated with a radiolabeled amino acid. The radiolabel may be used for both diagnostic and therapeutic purposes. For instance, the radiolabel may be used to detect FTC by x-ray, emission spectra, or other diagnostic techniques. Examples of labels for polypeptides include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I, and $^{32}$P.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The choice of a particular detectable marker (or effector molecule) depends, amongst other things, on the particular cell, the desired biological effect, and/or the detection method. Thus, for example, the effector molecule can be a fluorescent molecule can be used if visualization will use fluorescent light. Any effector molecule that can be detected, such as by using another antibody, can be utilized in the detection methods disclosed herein. This includes proteins, particles and other agents.

Detectable markers and effector molecules can be linked to an antibody or antigen binding fragment of interest using any number of means known to those of skill in the art. Both covalent and noncovalent attachment means may be used. The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

Thus, in several embodiments, the conjugate includes a linker that connects the effector molecule or detectable marker to the FTC-specific antibody or antigen binding fragment thereof. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15, amino acids long. In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker not released.

The average number of detectable marker moieties per antibody or antigen binding fragment in a conjugate can range, for example, from 1 to 20 moieties per antibody or antigen binding fragment. In certain embodiments, the average number of effector molecule or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments.

C. Polynucleotides and Expression

Nucleic acids molecules (for example, cDNA molecules) encoding the $V_H$ and $V_L$ amino acid sequences of antibodies, antigen binding fragments, and conjugates that specifically bind FTC are provided. Nucleic acids encoding these molecules can readily be produced by one of skill in the art, using the amino acid sequences provided herein (such as the CDR sequences and $V_H$ and $V_L$ sequences), sequences available in the art (such as framework or constant region sequences), and the genetic code. In several embodiments, a nucleic acid molecule can encode the $V_H$, the $V_L$, or both the $V_H$ and $V_L$ (for example in a bicistronic expression vector or as a scFv) of a disclosed antibody or antigen binding fragment. In several embodiments, the nucleic acid molecules can be expressed in a host cell (such as a mammalian cell) to produce a disclosed antibody or antigen binding fragment.

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence. In one non-limiting example, an isolated nucleic acid can encode an scFV, as disclosed herein.

In a non-limiting example, an isolated nucleic acid molecule encodes the $V_H$ of a disclosed antibody or antigen binding fragment and includes the nucleic acid sequence set forth as SEQ ID NO: 3, or a degenerate variant thereof. In a non-limiting example, an isolated nucleic acid molecule encodes the $V_L$ of a disclosed antibody or antigen binding fragment and includes the nucleic acid sequence set forth as SEQ ID NO: 4 or a degenerate variant thereof.

Nucleic acid sequences encoding the antibodies, antigen binding fragments, and conjugates that specifically bind FTC can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4$^{th}$ ed., Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The nucleic acid molecules can be expressed in a recombinantly engineered cell such as bacteria, plant, yeast, insect and mammalian cells. The antibodies, antigen binding fragments, and conjugates can be expressed as individual $V_H$ and/or $V_L$ chain (linked to an effector molecule or detectable marker as needed), or can be expressed as a fusion protein. Methods of expressing and purifying antibodies and antigen binding fragments are known and further described herein (see, e.g., Al-Rubeai (ed), *Antibody Expression and Production*, Springer Press, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed), Antibody Engineering, Vols. 1-2, $2^{nd}$ Ed., Springer Press, 2010; Harlow and Lane, *Antibodies: A Laboratory Manual*, $2^{nd}$, Cold Spring Harbor Laboratory, New York, 2013,). Optionally, a cleavage site can be included in a linker, such as a furin cleavage site.

The nucleic acid encoding a $V_H$ and/or the $V_L$ optionally can encode an Fc region (immunoadhesin). The Fc region can be an IgA, IgM or IgG Fc region. The Fc region can be an optimized Fc region, as described in U.S. Published Patent Application No. 20100/093979, incorporated herein by reference. In one example, the immunoadhesin is an $IgG_1$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to FTC and another antigen, such as, but not limited to CD3. The encoded $V_H$ and $V_L$ optionally includes a furin cleavage site between the $V_H$ and $V_L$ domains.

Those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibodies, antigen binding fragments, or conjugates can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes includes appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences includes a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or antigen biding fragment, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not include any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population includes mainly host cells (e.g., consisting essentially of) comprising the recombinant expression vector. The population also can be a clonal population of cells, in which all cells of the population are clones of a single host cell comprising a recombinant expression vector, such that all cells of the population include the recombinant expression vector. In one embodiment of the invention, the population of cells is a clonal population comprising host cells comprising a recombinant expression vector as described herein Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the antibodies, antigen binding fragments, and conjugates can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin.

Methods for expression of the antibodies, antigen binding fragments, and conjugates, and/or refolding to an appropriate active form, from mammalian cells, and bacteria such as *E. coli* have been described and are well-known, and are applicable to the antibodies disclosed herein. See, e.g., Harlow and Lane, *Antibodies: A Laboratory Manual*, $2^{nd}$, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

In addition to recombinant methods, the antibodies, antigen binding fragments, and/or conjugates can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology*. Vol. 2: *Special Methods in Peptide Synthesis*, Part A. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

D. Compositions

Compositions are provided that include one or more of the disclosed conjugates, antibodies, or antigen binding fragments, that specifically bind FTC, in a carrier (such as a pharmaceutically acceptable carrier). The compositions can be prepared in unit dosage forms for detection methods.

The compositions can include a solution of the conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody or antigen binding fragment or conjugate in these formulations can vary with the particular method of use selected and the subject's needs. Actual methods of preparing such forms are known, or will be apparent, to those skilled in the art.

Antibodies, antigen binding fragments, or conjugates may be provided in lyophilized form and rehydrated with sterile water before administration, although they are also provided in sterile solutions of known concentration. The antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the reconstitution of antibody or antigen binding fragment and conjugate drugs. Additional agents, including preservatives can be added.

E. Kits

Kits are also provided. For example, kits for detecting FTC in a biological sample form in a subject, or determining the dose of FTC for administration to a subject. The kits will typically include an antibody or antigen binding fragment that specifically binds FTC and/or a conjugate thereof. The kit can also include nucleic acids, vectors, or host cells for producing a monoclonal antibody or antigen binding fragment that specifically binds FTC.

More than one of the conjugates or antibodies or antigen binding fragments that specifically bind FTC can be included in the kit. Thus, in several non-limiting examples, the kit can include two or more antibodies that specifically bind FTC, or an antibody or antigen binding fragment that specifically binds FTC that is unlabeled and a conjugate thereof, or a combination thereof. In some embodiments, an antigen binding fragment or conjugate including an antigen binding fragment, such as an Fv fragment, is included in the kit. The kit can include a solid substrate, such as, but not limited to, polystyrene, cellulose or nitrocellulose, comprising FTC, such as attached to the surface. The kit can include a control, such as a specific amount of FTC. The kit can include a test strip, such as a test strip including FTC at one or more known concentrations at identifiable locations. In some embodiments, the test strip includes one, two or three concentrations of FTC at an identifiable location.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed FTC specific antibodies, antigen binding fragments, or conjugates. In several embodiments, the container may have an access port (for example the container may be an intravenous solution bag or a vial having a stopper pierceable by a hypodermic injection needle) so that a specific amount of antibody, antigen binding fragment, or conjugate can be withdrawn.

A label or package insert indicates that the composition is used for detecting FTC. The label or package insert typically will further include instructions for use of a disclosed FTC specific antibodies or fragments thereof, or conjugates thereof, for example. The package insert typically includes instructions customarily included in commercial packages of products that contain information about the indications, usage, contraindications and/or warnings concerning the use of such products. The instructional materials may be written, in an electronic form (such as a computer diskette or compact disk) or may be visual (such as video files).

The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. The kit can include solid substrates including a specified amount of FTC, or controls including defined amounts of FTC. Such kits and appropriate contents are well known to those of skill in the art.

F. Methods of Detection and Devices

The antibodies disclose herein specifically bind FTC and can be used to identify FTC in a sample, such as a biological sample. In some embodiments, the methods include contacting a biological sample with an antibody that specifically binds FTC to form an immune complex. The presence of the immune complex indicates that FTC was present in the biological sample, or the concentration of FTC present in the biological sample. The immunoassays that can be used in the methods disclosed herein include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, lateral flow assays (LEA) and microfluidic assays.

A biological sample can be obtained from a mammalian subject of interest, such as human. The biological sample can be cells, bodily fluids, such as blood (including dried blood), derivatives and fractions of blood (such as serum or plasma), hair, nails, cerebrospinal fluid, urine or sputum; as well as biopsied or surgically removed tissue, for example tissues that are unfixed, frozen, or fixed in formalin or paraffin. The biological sample can be from any organ. In some embodiments, the biological sample is blood, plasma, or serum. In other embodiments, the biological sample is hair or urine. In additional embodiments, the biological sample is obtained from a subject, and the presence of FTC is assessed in vitro.

The biological sample can be obtained from any subject of interest. In some embodiments, the subject has an HIV infection. In other embodiments, the subject does not have an HIV infection, such as a subject at risk for an HIV infection. Suitable subjects are being treated with a therapeutic or prophylactic protocol that includes FTC. Suitable subjects include who participate in risky sexual practices, drug users, or clinicians (for example, doctors, nurses, medical technicians and dentists) at risk for exposure to blood from HIV-infected patients, and are treated with a protocol including FTC.

In some embodiments, the subject has an HIV infection. The disclosed methods can be used to determine compliance with a therapeutic protocol for an existing HIV infection. The therapeutic protocol can have been prescribed, for example, for 1, 2, 3, 4, 5, 6, 7, 8, 9, 10, 15, 20, 25, 28, 30, 45, 60, 90, or 120 days. The protocol can include, for example, FTC and a tenofovir prodrug, such as TDF or TAF. The protocol can include, for example, TRUVADA®. The therapeutic protocol can include a therapeutically effective amount of a tenofovir prodrug, such as but not limited to, a therapeutically effective tenofovir alafenamide (TAF) or TDF, and therapeutically effective amount of elvitegravir (EVG). In other examples, the therapeutic protocol can include a therapeutically effective amount of a tenofovir prodrug, such as but not limited to, a therapeutically effective TAF or TDF, and a therapeutically effective amount of EVG, and optionally an effective amount of COBI.

In other embodiments, the subject does not have an HIV infection. The disclosed methods can be used to determine compliance with a PrEP protocol or a PEP protocol that includes FTC. The prophylactic protocol can be used, for example, for 1, 2, 3, 4, 5, 6, 7, 8, 9, 10, 15, 20, 25, 30, 45, 60, 90, or 120 days. The prophylactic protocol can be used before a potential exposure to HIV, such as 2, 4, 6, 8, 10, 12, 14, 16, 18, 20, 22, 24, 48, 60 or 70 hours before a potential exposure to HIV. The prophylactic protocol can include, for example, FTC and a tenofovir prodrug, such as TDF or TAF. The prophylactic protocol can include, for example, TRUVADA®. The prophylactic protocol can include a prophylactically effective amount of FTC, a tenofovir prodrug, such as but not limited to, a prophylactically effective TAF or TDF, and a prophylactically effective amount of EVG. In other examples, the prophylactic protocol can include a prophylactically effective amount of a tenofovir prodrug, such as but not limited to, a therapeutically effective TAF or TDF, and a prophylactically effective amount of EVG, and optionally a prophylactically effective amount of COBI.

U.S. Published Patent Application No. 2015/0105350, incorporated herein by reference, discloses the use of FTC, TAF and other tenofovir prodrugs, EVG, and COBI for the treatment of HIV infections. As disclosed in this published patent application the oral dose of TAF can be in the range from about 0.0001 to about 100 mg/kg body weight per day, for example, from about 0.01 to about 10 mg/kg body weight per day, from about 0.01 to about 5 mg/kg body weight per day, from about 0.5 to about 50 mg/kg body weight per day, from about 1 to about 30 mg/kg body weight per day, from about 1.5 to about 10 mg/kg body weight per day, or from about 0.05 to about 0.5 mg/kg body weight per day. As a non-limiting example, the daily candidate dose for an adult human of about 70 kg body weight will range from about 0.1 mg to about 1000 mg, or from about 1 mg to about 1000 mg, or from about 5 mg to about 500 mg, or from about 1 mg to about 150 mg, or from about 5 mg to about 150 mg, or from about 5 mg to about 100 mg, or about 10 mg, and may take the form of single or multiple doses. In one embodiment, the oral dose of TAF may be in the form of a combination of agents (e.g., TAF/FTC/EVG/COBI). Any of these doses can be used in the therapeutic or prophylactic protocol.

Exemplary dosages are (1) COBI: 10-500 mg, 50-500 mg, 75-300 mg, 100-200 mg, or 150 mg; (2) TAF: 1-60 mg, 3-40 mg, 5-30 mg, 8-20 mg, or 10 mg; (3) FTC: 10-500 mg, 50-500 mg, 75-300 mg, 150-250 mg, or 200 mg; and (4) EVG: 10-500 mg, 50-500 mg, 75-300 mg, 100-200 mg, or 150 mg. Tenofovir can be used in amounts of less than 300 mg, 200 mg or less and 100 mg or less. COBI can be used in amounts of 50-500 mg, 100-400 mg, 100-300 mg, and 150 mg. Any of these doses can be used in the therapeutic or prophylactic protocol.

Tenofovir (or a prodrug thereof, such as but not limited to, TDF or TAF) and COBI or pharmaceutically acceptable salt(s) thereof, can be co-administered with FTC. Tenofovir (or TDF, TAF, or another prodrug), COBI, FTC, and EVG can be co-administered. The agents can be administered in the same or different compositions for either therapeutic or prophylactic methods. Any of these compositions can be used in the therapeutic or prophylactic protocol.

The subject can have been administered 200 mg of FTC and 150 mg of EVG. The subject can have been administered 150 mg COBI, 100 mg or less tenofovir, 150 mg EVG, and 200 mg FTC. The method can include co-administering 150 mg COBI, 200 mg or less tenofovir, 150 mg EVG, and 200 mg FTC. The subject can have been administered 150 mg COBI, less than 300 mg tenofovir, 150 mg EVG, and 200 mg FTC. The subject can have been administered 150 mg COBI, 50 mg tenofovir, 150 mg EVG, and 200 mg FTC. In some specific non-limiting example, the subject can have been administered 150 mg EVG, 150 mg COB, 200 mg FTC, and 10 mg TAF. These compositions can be administered orally. See U.S. Published Patent Application No. 2015/0105350, incorporated herein by reference for additional dosing information. In some embodiments, GENOYA® is administered. Any of these doses can be used in the therapeutic or prophylactic protocol.

The biological sample can be obtained, for example, at 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours after administration of one therapeutically effective amount of prophylactically effective amount of FTC was (or was expected to be) administered to the subject. In some embodiments, the method can determine compliance with a therapeutic or prophylactic protocol.

These methods can include contacting the biological sample, or an extract thereof, with an antibody, antigen binding fragment or conjugate provided herein that specifically binds FTC to form an immune complex. The presence (or absence) of the immune complex is then detected. The presence (or absence) of the immune complex indicates the presence (or absence, respectively) of FTC. In some non-limiting examples, the amount of the immune complex is quantified to determine the amount of FTC present in the biological sample.

In further embodiments, the amount of the immune complex is compared to a negative control. An increase in the presence of this immune complex in the biological sample, compared to the presence of the immune complex in a control sample, such as a sample not contacted with the antibody or antigen binding fragment, a sample contacted with an unrelated antibody, or a reference standard, detects the presence of FTC in the biological sample. In yet other embodiments, the amount of the immune complex is compared to a positive control. The positive control can be: i) a standard value; ii) an amount of immune complex formed in the following contacting the antibody with a biological sample from a control subject known to be effectively treated with the therapeutic or prophylactic protocol comprising FTC, in the same reaction conditions; or iii) a sample matrix that includes a known amount of FTC.

In some embodiments, the antibody that specifically binds FTC or antigen binding fragment is conjugated to a detectable marker. In additional embodiments, the methods include the use of a second antibody that specifically binds the antibody that specifically binds FTC, antigen binding fragment thereof, or a conjugate including these molecules, for a sufficient amount of time to form an immune complex, and then detecting the presence of this immune complex. An increase in the presence of this immune complex in a biological sample (as described above) compared to the presence of the immune complex in a control sample. In some examples, the second antibody is conjugated to a detectable marker.

In some embodiments, the assay is a competitive binding assay. In particular embodiments, a method of determining if a subject is complying with a therapeutic or prophylactic protocol comprising emtricitabine (FTC), includes: contacting a solid support comprising FTC with a) a test biological sample from the subject obtained following a period of time for the administration of the therapeutic or prophylactic protocol to the subject and b) a monoclonal antibody or antigen binding fragment that specifically binds FTC disclosed herein, under conditions sufficient to form an immune complex, and quantitating an amount of immune complex bound to the solid support. Solid supports include, but are not limited to, cellulose, nitrocellulose and nylon.

In some non-limiting examples, the method also includes comparing the amount of the immune complex bound to the solid support to a control. If the amount of the immune complex bound to the solid support is the same or lower than the control, then the subject is complying with the therapeutic or prophylactic protocol. If the amount of the immune complex bound to the solid support is higher than the control, then the subject is not complying with the therapeutic or prophylactic protocol.

Suitable controls include, but are not limited to: i) a standard value or ii) an amount of immune complex bound to the solid support comprising FTC contacted with a) a biological sample from a control subject known to be effectively treated with the therapeutic or prophylactic protocol or a sample matrix including a known amount of FTC, and b) a monoclonal antibody or antigen binding fragment that specifically binds FTC disclosed herein, under the same conditions sufficient to form an immune complex.

Suitable detectable markers for the antibody, antigen binding fragment, or secondary antibody are described and known to the skilled artisan. For example, various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$. Another suitable detectable label is gold. Additional examples of labels are disclosed above; these labels can all be used in the disclosed methods.

In some embodiments, the assay is an enzyme-linked immunosorbant assay (ELISA) or a radioimmunoassay (RIA). In other embodiments the assay is a Western blot. In other embodiments the assay is a lateral flow or microfluidic assay. The antibodies that specifically bind FTC and conjugates thereof can be used in immunohistochemical assays. These assays are well known to one of skill in the art (see Harlow & Lane, *Antibodies, A Laboratory Manual*, Cold Spring Harbor Publications, New York (1988), for a description of immunoassay formats.

The disclosed methods include use on lateral flow assays and in microfluidic devices. Immunochromatographic assays fall into two principal categories: "sandwich" and "competitive." In general, sandwich immunochromatographic procedures call for mixing the sample that may contain FTC with the disclosed antibodies. These antibodies are mobile and typically are linked to a label or another signaling reagent, such as dyed latex, a colloidal metal sol, or a radioisotope. This mixture is then applied to a chromatographic medium containing a band or zone of immobilized antibodies to that bind the immune complex. The chromatographic medium often is in the form of a strip that resembles a dipstick. When the complex of the molecule to be assayed and the labeled antibody reaches the zone of the immobilized antibodies (that bind the complex) on the chromatographic medium, binding occurs and the bound, labeled antibodies are localized at the zone. This indicates the presence of the molecule to be assayed. This technique, and these immunoassay devices, can be used to obtain quantitative or semi-quantitative results. Examples of sandwich immunoassays performed on test strips are described in U.S. Pat. Nos. 4,168,146 and 4,366,241, which are incorporated herein by reference.

The chromatographic medium often is in the form of a strip that resembles a dipstick. When the reaches the zone of the immobilized antibodies (that bind the complex) on the chromatographic medium, binding occurs and the bound, labeled antibodies are localized at the zone. This indicates the presence of the molecule to be assayed. This technique, and these immunoassay devices, can be used to obtain quantitative or semi-quantitative results.

In competitive immunoassays, the label is typically a labeled FTC that competes with any unlabeled FTC present in the sample for binding to the disclosed antibody. In such competitive assays, the FTC and labeled FTC are simultaneously introduced to the disclosed antibody, such that these molecules compete for binding sites. Examples of competitive immunoassay devices are those disclosed by U.S. Pat. Nos. 4,235,601, 4,442,204 and 5,208,535, which are incorporated herein by reference.

Solid phase immunoassay devices, whether sandwich- or competition-type, provide sensitive detection of an analyte in a biological fluid sample. Solid phase immunoassay devices incorporate a solid support to an antibody or antigen is bound. Common early forms of solid supports were plates, tubes, or heads of polystyrene, which were known from the fields of radioimmunoassay and enzyme immunoassay. More recently, a number of porous materials such as nylon, nitrocellulose, cellulose acetate, glass fibers, and other porous polymers have been employed as solid supports. One of skill in the art can readily covalently bind a monoclonal antibody to these solid supports.

In some forms of dipstick assays, immunochemical components such as antibodies are bound to a solid phase. The assay device is "dipped" for incubation into a sample suspected of containing FTC. Enzyme-labeled antibody is then added, either simultaneously or after an incubation period. The device next is washed and then inserted into a second solution containing a substrate for the enzyme. The enzyme-label, if present, interacts with the substrate, causing the formation of colored products, which either deposit as a precipitate onto the solid phase or produce a visible color change in the substrate solution. European Publication No. EP-A 0 125 118 discloses an exemplary sandwich type dipstick immunoassay, and European Publication No. EP-A 0 282 192 discloses an exemplary dipstick device for use in competition type assays, such as the ones disclosed herein.

Flow-through type immunoassay devices (such as test strips) can obviate the need for incubation and washing steps associated with dipstick assays. U.S. Pat. No. 4,632,901 discloses a sandwich immunoassay device wherein antibody is bound to a porous membrane or filter to which a liquid sample is added. As the liquid flows through the membrane, target analyte binds to the antibody. The addition of sample is followed by addition of labeled antibody. The visual detection of labeled antibody provides an indication of the presence of target antigen analyte in the sample. This format can also be used with the assays disclosed herein. Migration assay devices usually incorporate within them reagents that have been attached to colored labels, thereby permitting visible detection of the assay results without addition of further substances. See, for example, U.S. Pat. No. 4,770,853; PCT Publication No. WO 88/08534; and European Publication No. EP-A 0 299 428, which are incorporated by reference. U.S. Pat. No. 5,451,504 provides a method with three specific zones (mobilization, trap and detection) each containing a different latex conjugate to yield a positive signal. The mobilization zone contains labeled antibody to bind the analyte (FTC in 30 the presently disclosed methods) in the sample. In the trap zone, unbound, labeled antibody is then trapped by immobilized analyte analog. The detection zone captures the labeled analyte-antibody complex. U.S. Pat. No. 6,001,658 discloses a test strip device with a diffusible, labeled binding partner that binds with analyte (FTC using the presently disclosed methods), an immobilized analyte, and a detection area containing an immobilized antibody. Additional lateral flow apparatuses are disclosed in U.S. Pat. No. 6,699,722, which is also incorporated by reference. These formats of immunoassay devices are all of use with the antibodies and methods disclosed herein.

Figure 5:
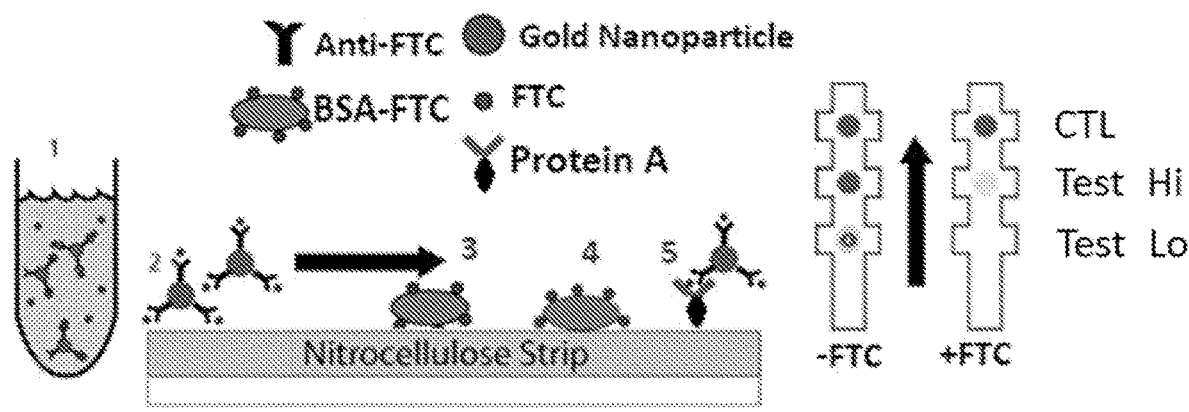
FIG. 5. Schematic drawing of an exemplary lateral flow assay (LFA).
Figure 6:
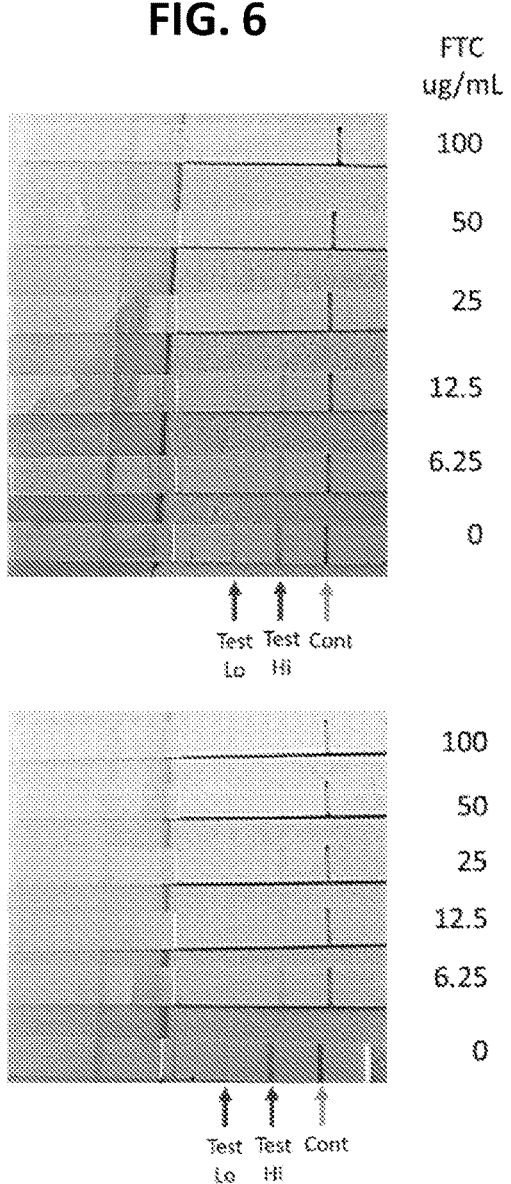
FIG. 6. Exemplary results from a lateral flow assay using decreasing concentration of FTC.

In one embodiment, the sample that may contain FTC is mixed with the disclosed antibodies that are mobile and typically are linked to a label or another signaling reagent, such as dyed latex, a colloidal metal sol, or a radioisotope, to form a labeled immune complex. In a non-limiting example, the antibodies are labeled with gold. However, any label (see above) can be utilized. This mixture, which includes the immune complex is can be applied to a solid support, such as, but not limited to, nitrocellulose or other material containing a band or zone of FTC. The solid support, such as nitrocellulose, can include more than one band or zone of FTC that represents different concentrations. For example, there can be a high and a low concentration of FTC. The nitrocellulose can include 1, 2, 3, 4, or five different concentrations of FTC, ordered from the lowest concentration to the highest concentration from where the sample is applied. If there is more antibody than FTC in the sample, the labeled antibody will bind to the FTC present on the solid support, such as nitrocellulose. In some embodiments, a low and a high concentration of FTC is present on the solid support at an addressable location. If no FTC is present in the sample, the labeled antibody will bind at the addressable location of both the high and the low concentrations. If a high amount of FTC is present in the sample, the labeled antibody will not bind the FTC at the addressable locations. If a low amount of FTC is present in the sample, the labeled antibody will bind at both addressable locations. In some embodiments, a positive control, for example a reagent that binds all antibodies (for example, ConA or an anti-immunoglobulin antibody), is also included at an addressable location. Exemplary immunoassay devices, in the form of test strips, are shown in FIGS. 5 and 6.

Methods are also disclosed herein for determining the effectiveness of a dose, or the duration of a dose, of FTC. In some embodiments, the subject has HIV, and FTC is administered in a therapeutic protocol. In other embodiments, the subject does not have an existing HIV infection, and the FTC is administered as a PrEP or a PEP. The methods can be used to determine the lowest effective therapeutic dose of FTC of use for treating a subject. The methods can be used to determine the lowest effective therapeutic dose of FTC of use for treating a subject. These methods include detecting FTC in a biological sample from the subject administered the FTC. In some embodiments, the quantity and molar fraction of FTC in the biological sample is determined following FTC administration to the subject. This fraction may be either increased or decreased as compared to a control.

In some embodiments, the presence and/or amount of FTC is determined in a sample from a subject administered a dose of FTC as part of therapy, PEP or PrEP. The method includes contacting a biological sample from a subject administered the dose of FTC, such as, but not limited to, a blood, serum or urine sample, with an antibody, or antigen binding fragment thereof, that specifically FTC, in order to form an immune complex. The presence (or amount) of the immune complex indicates the effectiveness of the treatment. The amount of the immune complex can be quantitated.

In additional embodiments, the amount of the immune complex can be compared to a control, such as the amount of FTC in a biological sample taken prior to the administration. In some embodiments, an increase in the amount of FTC in the sample, indicates that the first dose of the therapeutic agent is effective for the treatment, and/or that the therapeutic agent has been administered for a sufficient duration of time to treat the subject. In other embodiments, an increase or no change in the amount of the immune complex, as compared to a control, indicates that the first dose of FTC is effective for the treatment and/or that the FTC has been administered for a sufficient duration of time to treat the subject. In other embodiments, a decrease in the amount of the immune complex, as compared to a control, indicates that the first dose of FTC is not effective for the treatment and/or that the FTC has not been administered for a sufficient duration of time to treat the subject.

In some embodiments, the dose of FTC is decreased based on the results of the assay, and a second lower dose of FTC is administered to the subject. In additional embodiments, these methods can be used to determine the lowest effective dose of FTC of use to treat the subject. In yet other embodiments, when the amount of FTC in the biological sample is too low (not sufficient), the dose of the FTC is increased based on the results of the assay. In other examples, and additional higher dose of FTC is administered to the subject.

Thus, in additional embodiments, the method can include administering to the subject a second dose of the therapeutic agent, wherein the second dose is the same, greater, or less than the first dose of the therapeutic agent. The presence (or amount) of FTC is then detected in a second biological sample obtained from the subject after administration of the second dose of the therapeutic agent. The biological sample is then contacted with an antibody or antigen binding fragment thereof, that specifically binds FTC to form an immune complex. The amount of the immune complex can be quantitated. The presence (or amount), or absence, of the immune complex indicates the effectiveness of the treatment.

The amount of the immune complex can be compared to a control, such as the amount of FTC in a sample taken from the subject after the first dose of FTC, a sample matrix including a known amount of FTC, or a standard value.

The method can be repeated 1, 2, 3, 4, 5, 6, 7, 8, 9, 10 or more times to determine the lowest dose of FTC that is effective for treating the subject, and/or the shortest duration of administration that is effective for treating the subject, or for preventing an HIV infection. The methods can also be used over the course of a therapeutic or prophylactic protocol to monitor the efficacy.

This disclosure is illustrated by the following non-limiting examples.

EXAMPLES

Example 1

Conjugation of FTC to Proteins

FTC was attached to a heptanoic acid linker via the available hydroxyl group (FIG. 1) (Sigma-Alrich, now Millipore Sigma, St. Louis, Mo.) yielding the drug-linker compound with a carboxyl group for conjugation of other molecules away from the FTC attachment. A six amino acid peptide (beta-alanine-arginine-glycine-cysteine-glycine-serine-$NH_2$; hereafter referred to as "peptide") was attached to heptanoic acid to provide an available sulfhydryl group for conjugation to limulus polyphemus hemocyanin II (LPH) to serve as the immunogen and to bovine serum albumin (BSA) for use in screening and identifying potential hybridomas secreting antibodies to FTC. See FIG. 1.

Example 2

Generation of Monoclonal Antibodies (Mabs) to FTC

Mouse Mabs to FTC were developed at Precision Antibody (Columbia, Md.) using standard techniques. Briefly, BALB/c mice were inoculated with the FTC-LPH conjugate. Clones that were reactive to the FTC-LPH conjugates and not the carrier proteins were expanded in cultures for 2-3 weeks. Clonal supernatants with reactive Mabs were subsequently purified by protein A affinity chromatography (MAPS II system, Bio-Rad Laboratories, Hercules, Calif.). The Mabs were dialyzed against a 10 mM potassium phosphate buffer pH 7.4 or with phosphate buffered saline (PBS) and the concentration of antibody adjusted to 1 mg/ml. Mabs were aliquoted in 1 ml volumes and lyophilized for long term storage.

Purified Mabs were evaluated for their ability to bind free FTC in solution using a competitive enzyme immunoassay (EIA) (see competitive assay section below). Antibody subclass was determined by Precision for the specific antibodies selected.

Example 3

FTC Screening Assay

An assay was developed to screen the Mabs for reactivity to the FTC conjugates. Microtiter plates were coated with the following reagents: FTC-peptide-dextran, FTC-peptide, FTC-peptide-LPH, FTC-peptide-BSA, FTC heptanoic acid, peptide only, peptide-LPH, peptide-BSA, BSA, LPH, and normal mouse serum (NMS). All compounds were diluted into sodium bicarbonate buffer, pH 9.6, to a concentration of 5 ug/ml; NMS was diluted 1:15. One hundred microliters of each solution was added to a column of the microtiter plate such that each row of the plate allowed the testing of a single clonal supernatant against all of the compounds in a single run. Plates were incubated at 4° C. overnight and then washed 3× with phosphate-buffered saline (PBS) containing 0.05% Tween 20 (PBS-T). Plates were blocked with PBS containing 0.5% nonfat dry milk for 1 hour at 37° C., washed 3×, and dried at 37° C. for 30 minutes. Prepared plates were covered with an adhesive seal, placed into a moisture resistant bag, and stored in a dessicant chamber at 20-24° C. until use.

Clonal supernatants (100 ul) were added to the appropriate wells and incubated at 37° C. for 1 hr. Plates were washed 3× with PBS-T. Captured antibodies were identified using a goat anti-mouse IgG horseradish peroxidase conjugate (Seracare, Milford, Mass.) diluted 1:2,5000 in PBS-T (100 ul/well) and incubated at 37° C. for 1 hr. Plates were washed 3× and 100 ul of detection reagent (single component tetramethyl benzidine/hydrogen peroxide) added to each well. Plates were incubated at 25° C. for 30 minutes; the reaction was stopped by the addition of 100 ul of 1N sulfuric acid. Absorbance was measured at 450 nm with a 630 nm reference.

Persistently reactive clones were further tested using FTC-peptide coated plates. Supernatants were incubated with various concentrations of free FTC for 30 minutes at 25° C. and then the assay conducted as described above. Antibodies that yielded a reduction in absorbance versus the sample containing no FTC were selected for optimization in a FTC detection assay. From this detailed screening, one Mab (5D2) was identified that was competitively reactive with FTC and did not react with the carrier proteins.

Example 4

Competitive Indirect EIA and Specificity of Mab 5D2

Because FTC is an analog of cytidine, a competitive indirect EIA was used to evaluate the reactivity of 5D2 to naturally occurring structural analogs consisting of nitrogenous nucleic acid bases, ribonucleosides, and deoxyribonucleosides, including cytidine, cysotine, deoxycytidine, adenine, adenosine, deoxyadenosine, guanine, guanosine, deoxyguanosine, thymine, 5-methyluridine, thymidine, uracil, uridine, and deoxyuridine. For the competitive assay, the concentrations of these analogs ranged from 12 to 1,000 ug/ml which is similar to the range of FTC found in urine. Reactivity was not detected to all of these naturally occurring analogs using this EIA.

Figure 4:
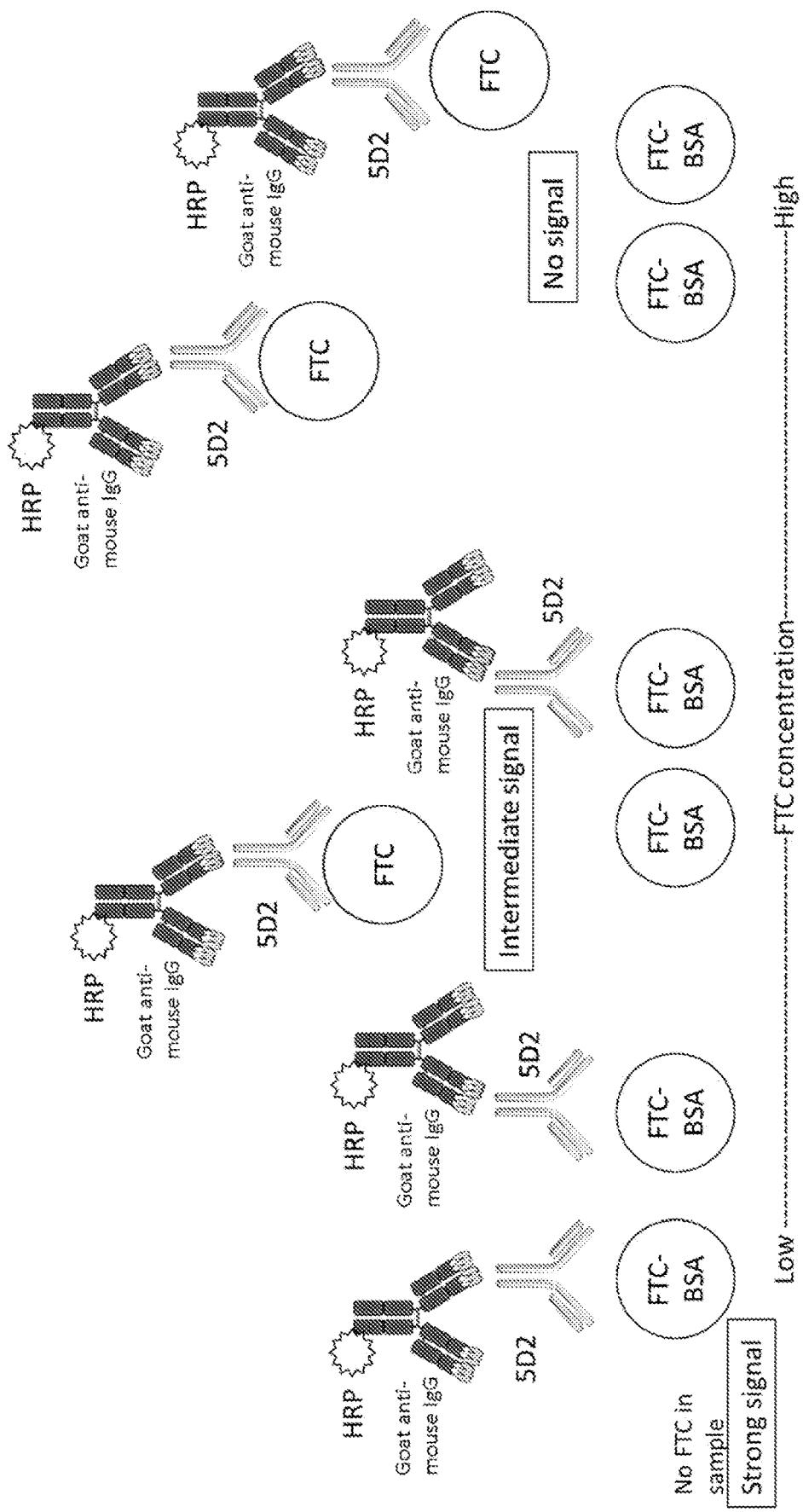
FIG. 4. Schematic drawing of an exemplary competitive assay.

The assay described here was optimized further to develop a semi-quantitative determination of FTC in buffer and in urine specimens. See FIG. 4 for a schematic diagram of an exemplary assay.

Example 5

Detection of FTC Spiked into Buffer

FTC conjugated to the heptanoic acid peptide construct was coated onto microtiter plates (110 µl/well) at 100 ng/ml and incubated overnight at 4° C. The plates were washed 4× with PBS-T (300 µl/well each wash) and were blocked with 3% BSA in PBS for 1 hr at 37° C. Coated plates were air dried for 1 hr and then placed in moisture resistant bags with desiccant for storage.

FTC was diluted into PBS-T containing 0.5% BSA and the 5D2 antibody (diluted 1:1,000). The mixture was allowed to react at ambient temperature for 1 hr and then was added to the microtiter plate (100 µl/well) for 1 hr at 37° C. The plates were washed and captured antibody was identified using the goat anti-mouse IgG HRP (100 ul) for 1 hr at 37° C. TMB substrate was added and allowed to react for 30 min at 25° C. and then stopped with the addition of 100 ul of 1N $H_2SO_4$. Detection and reading was performed as described above.

Figure 2A:
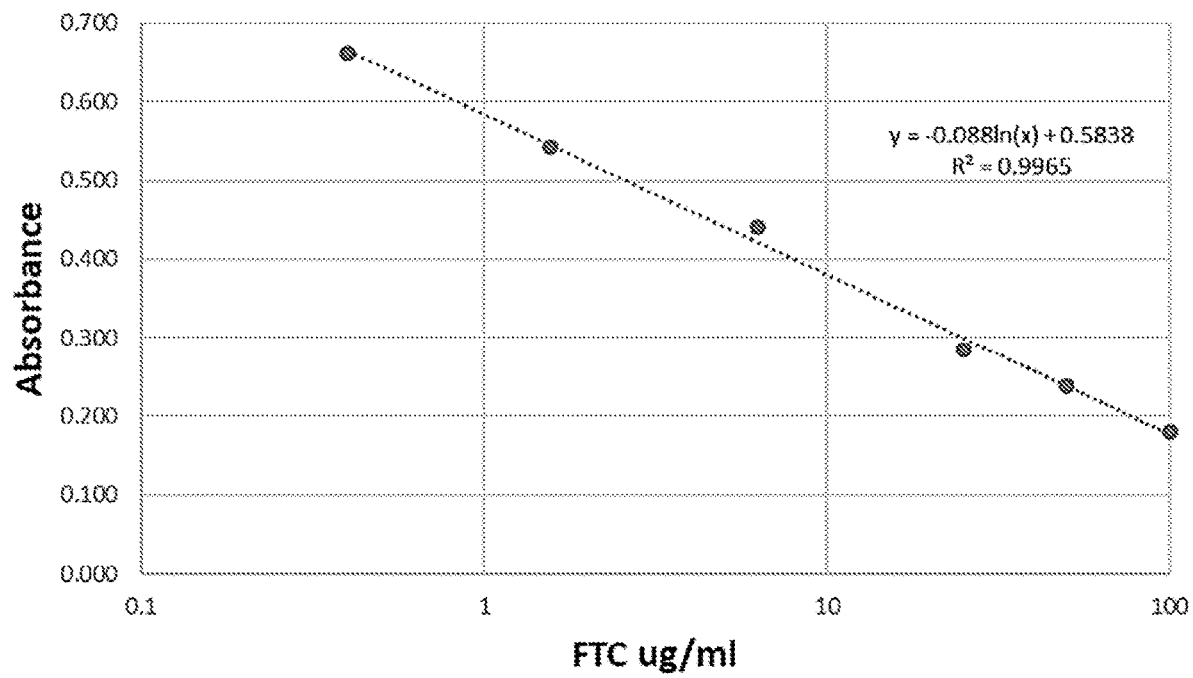
FIG. 2A. Dynamic linear range of competitive indirect EIA for FTC detection in buffer.

The dynamic linear range for FTC detection was from 100 µg/ml to 1 µg/ml well, within the expected range of FTC in urine (FIG. 2A). The lower limit of FTC detection is ~1 µg/ml.

Example 6

Specificity

The monoclonal antibody 5D2 was tested for cross-reactivity. 5D2 was determined to be specific for FTC, and to not bind to the following compounds:
Lamivudine (3TC), an antiretroviral drug that is structurally similar to FTC.
FTC-Triphosphate
FTC-Diphosphate
Cytidine
Deoxycytidine
Deoxyuridine
Guanosine
Deoxyguanosine
Deoxyadenosine
Adenosine
Thymidine
Uridine
Deoxyuridine
5-Methyluridine Example 7

Lateral Flow Assay

An exemplary lateral flow assay is shown in FIG. 5. Results are provided in FIG. 6.
1. The patient's sample is mixed with gold-conjugated anti-FTC antibody (clone 5D2, the gold nanoparticle is what provides the color on the strip)
2. Sample+anti-FTC conjugate is applied to the nitrocellulose membrane strip and flows first to the low FTC concentration test line
3. The low FTC concentration test line (low level FTC) has little FTC conjugated to BSA such that a small amount of FTC in the specimen will prevent the gold anti-FTC antibody from binding this line
4. The high concentration test line (high level FTC) requires that a higher amount of FTC is present (equivalent to a dose taken just a shortly before he specimen is collected) in order to prevent the gold anti-FTC antibody from binding this line
5. Control line (Protein A, can bind free gold conjugated anti-FTC) non-specifically binds antibody and is verification that the sample flowed appropriately across the strip. The absence of a colored line at either test position indicates sufficient FTC was present in the specimen to prevent gold anti-FTC antibody from binding the line.

Example 6

Optimized Competitive Indirect EIA and Assay Performance Data

The 5D2-based competitive assay for FTC was also detected FTC in urine. FTC is excreted in urine unchanged at a much higher concentration (1-500 µg/ml) than is found in serum or plasma (1-300 ng/ml). Urine is easier, more convenient, and less costly to collect than blood.

Figure 2B:
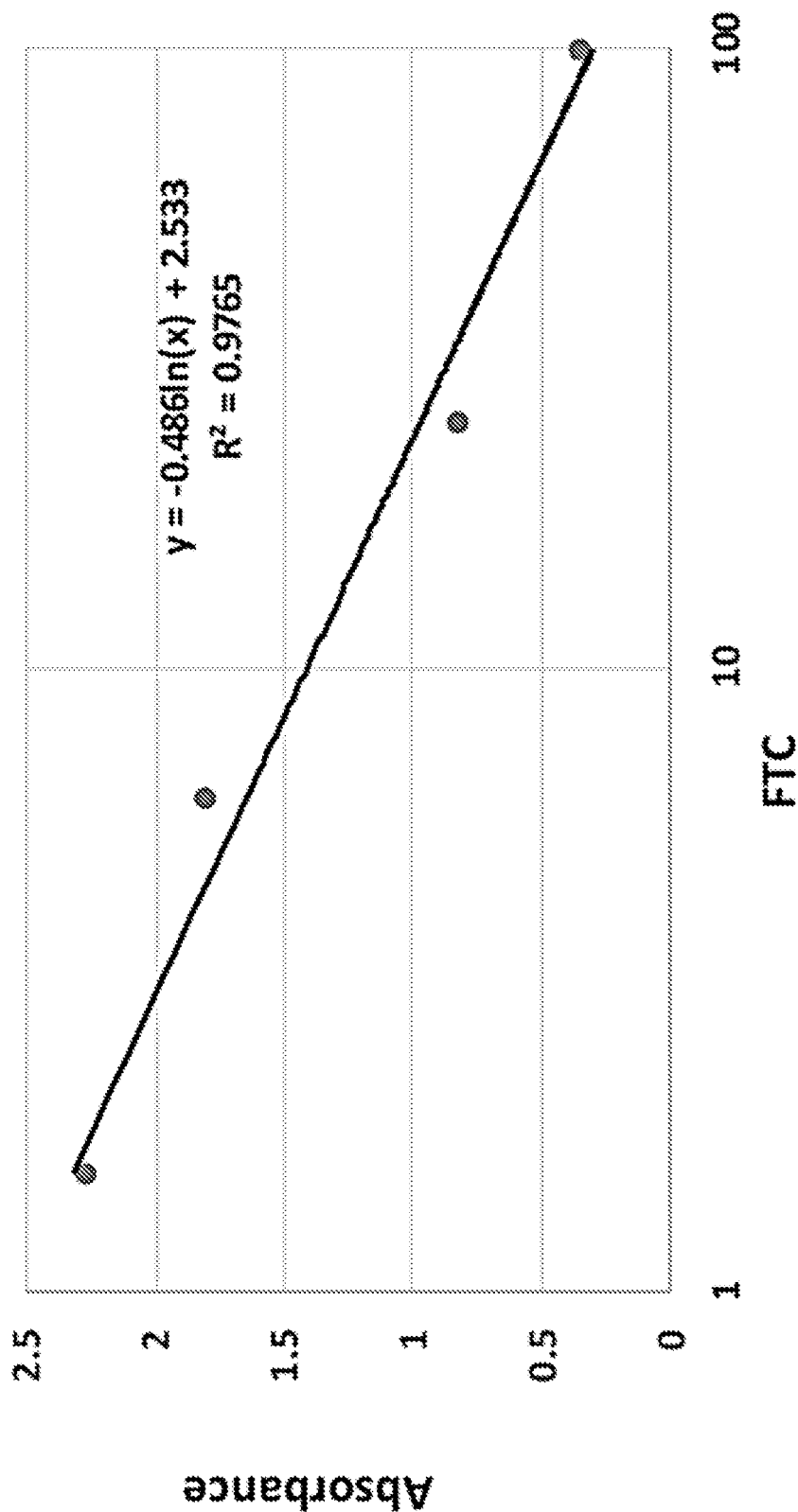
FIG. 2B. Dynamic linear range of the assay for FTC detection in urine.

For routine FTC detection in urine, the assay was conducted as described for buffer except using urine diluted 1:4 in 0.1M Tris-HCl pH 8.0 plus 1% BSA (effective limit of detection ~5 µg/ml). For optimization purposes, urine from a single donor were used and spiked FTC into the specimens. After assay reproducibility was established, the testing was repeated using five additional urine samples and achieved similar results. Results are shown in FIG. 2B.

Example 7

Sequencing

Sequencing strategy—FTC (5D2) monoclonal antibody sequences were obtained using two methods: a) Trypsin digestion and amino acid sequencing using a nanoLC-MS/MS system conducted at CDC, and b). rapid amplification of DNA ends (5'-RACE) conducted at Antibody Design Labs (11175 Flintkote Ave. Suite B, San Diego, Calif. 92121; Phone: 858-480-6213) to generate nucleotide sequences of heavy and light chain.

Sequences—
a) MS/MS—the protein coverage (minus the leader/signal peptide) is summarized below:
Heavy Chain
Fully Tryptic (77.0%):

```
                                              (SEQ ID NO: 1)
QVQLQQPGAE LVKPGASVKV SCKASGYTFT SYWMHWVKQR

PGQGLEWIGR IHLSDSDTNY NQNFKDKATL TVDKSSRTAH

MHLSSLTSAD SAVYYCAMGG TFQSNYDTYW GQGTLVTVSA

AKTTPPSVYP LAPGCGDTTG SSVTLGCLVK GYFPESVTVT

WNSGSLSSSV HTFPALLQSG LYTMSSSVTV PSSTWPSQTV

TCSVAHPASS TTVDKKLEPS GPISTINPCP PCKECHKCPA

PNLEGGPSVF IFPPNIKDVL MISLTPKVTC VVVDVSEDDP

DVRISWFVNN VEVHTAQTQT HREDYNSTIR VVSALPIQHQ

DWMSGKEFKC KVNNKDLPSP IERTISKIKG LVRAPQVYIL

PPPAEQLSRK DVSLTCLVVG FNPGDISVEW TSNGHTEENY

KDTAPVLDSD GSYFIYSKLD IKTSKWEKTD SFSCNVRHEG

LKNYYLKKTI SRSPGK
```

Semi-Tryptic (91.4%):

```
                                              (SEQ ID NO: 1)
QVQLQQPGAE LVKPGASVKV SCKASGYTFT SYWMHWVKQR

PGQGLEWIGR IHLSDSDTNY NQNFKDKATL TVDKSSRTAH

MHLSSLTSAD SAVYYCAMGG TFQSNYDTYW GQGTLVTVSA

AKTTPPSVYP LAPGCGDTTG SSVTLGCLVK GYFPESVTVT

WNSGSLSSSV HTFPALLQSG LYTMSSSVTV PSSTWPSQTV

TCSVAHPASS TTVDKKLEPS GPISTINPCP PCKECHKCPA

PNLEGGPSVF IFPPNIKDVL MISLTPKVTC VVVDVSEDDP

DVRISWFVNN VEVHTAQTQT HREDYNSTIR VVSALPIQHQ

DWMSGKEFKC KVNNKDLPSP IERTISKIKG LVRAPQVYIL

PPPAEQLSRK DVSLTCLVVG FNPGDISVEW TSNGHTEENY

KDTAPVLDSD GSYFIYSKLD IKTSKWEKTD SFSCNVRHEG

LKNYYLKKTI SRSPGK
```

Light Chain
Fully Tryptic (80.3%):

```
                                              (SEQ ID NO: 2)
DIQMTQSPAS LSASVGETVT ITCRASGNIH NYLAWYQQKQ

GKSPQLLVYN AKTLTDGVPS RFSGSGSGTQ YSLKINSLQP

EDFGNYYCQH FLYTPYTFGG GTKLEMRRAD AAPTVSIFPP

SSEQLTSGGA SVVCFLNNFY PKDINVKWKI DGSERQNGVL

NSWTDQDSKD STYSMSSTLT LTKDEYERHN SYTCEATHKT

STSPIVKSFN RNEC
```

Semi-Tryptic (98.6%):

```
                                              (SEQ ID NO: 2)
DIQMTQSPAS LSASVGETVT ITCRASGNIH NYLAWYQQKQ

GKSPQLLVYN AKTLTDGVPS RFSGSGSGTQ YSLKINSLQP

EDFGNYYCQH FLYTPYTFGG GTKLEMRRAD AAPTVSIFPP

SSEQLTSGGA SVVCFLNNFY PKDINVKWKI DGSERQNGVL

NSWTDQDSKD STYSMSSTLT LTKDEYERHN SYTCEATHKT

STSPIVKSFN RNEC
``` b) 5' RACE—
Heavy Chain Isotype: mouse IgG2b, first half of the sequence of CH1 had no mutation.
Nucleotide Sequence:

```
                                              (SEQ ID NO: 3)
ATGAGATGGAGCTGTCTCATCCTCTTCTTGTTAGCAACAACTCCAGGTG

TCCACTCCCAGGTCCAACTTCAGCAGCCTGGGGCTGAACTGGTGAAGCC

TGGGGCTTCAGTGAAGGTGTCCTGCAAGGCATCTGGCTACACCTTCACC

AGCTACTGGATGCACTGGGTGAAGCAGAGGCCTGGCCAAGGCCTTGAGT

GGATTGGAAGGATTCATCTTTCTGATAGTGATACTAACTACAATCAAAA

CTTCAAGGACAAGGCCACATTGACTGTAGACAAATCCTCCCGCACAGCC

CACATGCATCTCAGCAGCCTGACATCTGCGGACTCTGCGGTCTATTATT

GTGCAATGGGGGGGACCTTCCAGAGTAACTACGATACTTACTGGGGCCA

AGGGACTCTGGTCACTGTCTCTGCA
```

Amino Acid Sequence:
Leader
MRWSCLILFLLATTPGVHS (SEQ ID NO: 5)
VDJ (SEQ ID NO: 6)
QVQLQQPGAELVKPGASVKVSCKASGYTFTSYWMHWVKQRPGQGLEWIG

RIHLSDSDTNYNQNFKDKATLTVDKSSRTAHMHLSSLTSADSAVYYCAM

GGTFQSNYDTYWGQGTLVTVSA

Analysis
Variable domain: IGHV1-74*01
Joining region: IGHJ3*01
Light Chain
Isotype: mouse Kappa
Nucleotide Sequence:

(SEQ ID NO: 4)
ATGAGTGTGCTCACTCAGGTCCTGGCGTTGCTGCTGCTGTGGCTTACAG

GTGCCAGATGTGACATCCAGATGACTCAGTCTCCAGCCTCCCTATCTGC

ATCTGTGGGAGAAACTGTCACCATCACATGTCGAGCAAGTGGGAATATT

CACAATTATTTAGCATGGTATCAGCAGAAACAGGGAAAATCTCCTCAGC

TCCTGGTCTATAATGCAAAAACCTTAACAGATGGTGTGCCATCAAGGTT

CAGTGGCAGTGGATCAGGAACACAATATTCTCTCAAGATCAACAGCCTG

CAGCCTGAAGATTTTGGGAATTATTACTGTCAACATTTTTTGTATACTC

CTTACACGTTCGGAGGGGGGACCAAGCTGGAAATGAGA

Amino Acid Sequence:
Leader
MSVLTQVLALLLLWLTGARC (SEQ ID NO: 7)
VJ (SEQ ID NO: 8)
DIQMTQSPASLSASVGETVTITCRASGNIHNYLAWYQQKQGKSPQLLVY

NAKTLTDGVPSRFSGSGSGTQYSLKINSLQPEDFGNYYCQHFLYTPYTF

GGGTKLEMR.

Analysis:
Variable domain: IGKV12-41*01
Joining region: IGKJ2*01
Comparison of MS/MS and 5' RACE amino acid sequences—an alignment of the sequences showed 100% identity of the overlapping MS/MS and 5'RACE regions (represented by dots in the alignment), see FIG. 3.

Sequence analyses—a) Two methods (KABAT and IMGT) were used to identify the light and heavy chain complementarity determining regions (CDRs) using the NCBI website IGblast site which uses only nucleotide sequences, see FIG. 3. The website Paratome (ofranlab.org/paratome/) was also used to identify Antigen Binding Regions (ABRs), which are similar to CDRs (and are referred to as CDRs in the claims below). For this analysis, the amino acid (AA) sequences inferred from the nucleotide sequences of the monoclonal antibody 5D2 and the AA sequences determined using MS/MS were used. ABRs and IMGT/Kabat CDRs partially overlap, as they contain antigen binding residues within a given antibody. While IMGT/KABAT CDRs are considered a proxy for the recognition and binding site, the Paratome program is aimed specifically at identifying these residues. All three methods identified overlapping regions. The sequences below were determined by 5'RACE and MS/MS.

i) Paratome 5' RACE
>5D2 VL (Light Chain)

DIOMTOSPAS LSASVGETVT ITCRAS*GNIH NYLA*WYQQKQ

GKSPQ*LLVYN AKTLTD*GVPS RFSGSGSGTQ YSLKINSLQP

EDFGNYYC*QH FLYTPY*TFGG GTKLEMR ((amino acids 1-107 of SEP ID NO: 2)

ABR1: GNIHNYLA (27-34 of SEQ ID NO: 2)
ABR2: LLVYNAKTILTD (46-56 of SEQ ID NO: 2)
ABR3: QHFLYTPY (89-96 of SEQ ID NO: 2)

>5D2_VH (Heavy Chain)

QVQLQQPGAE LVKPGASVKV SCKASGYTFT *SYWMH*WVKQR

PGQGLE*WIGR IHLSDSDTNY* NQNFKDKATL TVDKSSRTAH

MHLSSLTSAD SAVYYCA *MGG TFQSNYDTY* W GQGTLVTVSA (amino acids 1-120 of SEQ ID NO: 1)

ABR1: YTFTSYWMH (27-35 of SEQ ID NO: 1)
ABR2: WIGRIHLSDSDTNY (47-60 of SEQ ID NO: 1)
ABR3: MGGTFQSNYDTY (98-109 of SEQ ID NO: 1)

ii) Paratome MS/MS
>5D2 VH_Fully_Tryptic (Heavy Chain)

(SEQ ID NO: 1)
QVQLQQPGAE LVKPCIASIIKV SCKASGYTFT *SYWMH*WVKQR PGQGLE*WIRG

*IHLSDSDTNY* NQNFKDKATL TVDKSSRTAH MHLSSLTSAD SAVYYCA*MGG

TFQSNYPTYW* GQGTUITVSA AKTTPPSVYP LAPGCGDTTG SSVTLGCLVK

GYFPESVTV WNSGSLSSSV HTFPALLQSG LYTMSSSVTV PSSTWPSQTV

TCSVAHPASS TTVDKKLEPS GPISTINPCP PCKECHKCPA PNLEGGPSVF

IFPPNIKDVL MISLTPKVTC VVVDVSEDDP DVRISWFVNN VEVHTAQTQT

HREDYNSTIR VVSALPIQHQ DWMSGKEFK CKVNNKDLPS PIERTISKIK

GLVRAPQVYI LPPPAEQLSR KDVSLTCLVV GFNPGDISVE WTSNGHTEEN Y

KDTAPVLD SDGSYFIYSK LDIKTSKWEK TDSFSCNVRH EGLKNYYLKK

TISRSPGK

ABR1: YTFTSYWMH (27-35 of SEQ ID NO: 1)
ABR2: WIGRIHLSDSDTNY (47-60 of SEQ ID NO: 1)
ABR3: MGGTFQSNYDTY (98-109 of SEQ ID NO: 1)

CDR1=31-36 of SEQ ID NO: 1
CDR2=50-66 of SEQ ID NO: 1 CDR3=99-109 of SEQ ID NO: 1

(SEQ ID NO: 2)
```
DIQMTQSPAS LSASVGETVT ITCRASGNIH NYLAWYOOKO GKSPOLLVYN

AKTLTDGVPS RFSGSGSGTQ YSLKINSLQP EDFGNYYCQH FLYTPYTFGG

GTKLEMRRAD AAPTVSIFPP SSEQLTSGGA SVVCFLNNFY PKDINVKWKI

DGSERQNGVL NSWTDQDSKD STYSMSSTLT LTKDEYERHN SYTCEATHKT

STSPIVKSFN RNEC
```

ABR1: GNIHNYLA (27-34 of SEQ ID NO: 2)
ABR2: LLVYNAKTLTD (46-56 of SEQ ID NO: 2)
ABR3: QHFLYTPY (89-96 of SEQ ID NO: 2)
Legend:
Heavy chain: ABR1 ABR2 ABR3 | Light chain: ABR1 ABR2 ABR3

Kabat and IMGT CDRs are listed below. These can be determined by IgBLAST, available on the internet through NCBI. See also Ye et al., Nucl. Acids Res. 41 (Web Server Issue): W34-40, ePub May 13, 2013, incorporated by reference.

VL Kabat aa locations:
CDR1=24-34 of SEQ ID NO: 2
CDR2=50-56 of SEQ ID NO: 2
CDR3=89-97 of SEQ ID NO: 2
VL IMGT aa locations:
CDR1=27-32 of SEQ ID NO: 2
CDR2=50-52 of SEQ ID NO: 2
CDR3=89-96 of SEQ ID NO: 2.
VH Kabat aa locations:
CDR1=31-36 of SEQ ID NO: 1
CDR2=50-66 of SEQ ID NO: 1
CDR3=99-109 of SEQ ID NO: 1
VH IMGT aa locations:
CDR1=26-32 of SEQ ID NO: 1
CDR2=51-58 of SEQ ID NO: 1
CDR3=97-109 of SEQ ID NO: 1

BLAST analyses were performed for the VL and VH amino acid sequences translated from the 5' RACE nucleotide sequences and using the MS/MS amino acid sequences. The results showed: 1) no identical sequences were found and 2) the VH is more divergent than VL against the AA sequences at GENBANK®.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of the following claims.

We claim:

1. An isolated monoclonal antibody or antigen binding fragment thereof comprising a heavy chain variable domain and a light chain variable domain,
   wherein the heavy chain variable domain comprises a heavy chain complementarity determining region (HCDR)1, an HCDR2 and an HCDR3, and wherein the light chain variable domain comprises a light chain complementarity determining region (LCDR)1, an LCDR2 and an LCDR3,
   wherein the heavy chain variable domain comprises the HCDR1, HCDR2 and HCDR3 of SEQ ID NO: 1 as determined using a method of Paratome, Kabat, Chothia or IMGT, and wherein the light chain variable domain comprises the LCDR1, LCDR2 and LCDR3 of SEQ ID NO: 2, as determined using the method of Paratome, Kabat, Chothia or IMGT, and wherein the HCDR1, HCDR2, HCDR3, HCDR3, LCDR1, LCDR2 and LCDR3 are determined using the same method,
   and wherein the monoclonal antibody specifically binds emtricitabine (FTC).

2. The isolated monoclonal antibody or antigen binding fragment of claim 1, wherein the HCDR1 comprises the amino acids 27 to 35 of SEQ ID NO: 1, the HCDR2 comprises amino acids 47 to 60 of SEQ ID NO: 1, and the HCDR3 comprises amino acids 98 to 109 of SEQ ID NO: 1, and wherein the LCDR1 comprises amino acids 27 to 34 of SEQ ID NO: 2, the LCDR2 comprises amino acids 46 to 56 of SEQ ID NO:2, and the LCDR3 comprises amino acids 89 to 96 of SEQ ID NO: 2.

3. The isolated monoclonal antibody or antigen binding fragment of claim 1, wherein the HCDR1 comprises amino acids 31 to 36 of SEQ ID NO: 1, the HCDR2 comprises amino acids 50 to 66 of SEQ ID NO: 1, and the HCDR3 comprises amino acids 99 to 109 of SEQ ID NO: 1, and wherein the LCDR1 comprises amino acids 24 to 34 of SEQ ID NO: 2, the LCDR2 comprises amino acids 50 to 56 of SEQ ID NO:2, and the LCDR3 comprises amino acids 89 to 97 of SEQ ID NO: 2.

4. The isolated monoclonal antibody or antigen binding fragment of claim 1, wherein the HCDR1 comprises amino acids 26 to 32 of SEQ ID NO: 1, the HCDR2 comprises amino acids 51 to 58 of SEQ ID NO: 1, and the HCDR3 comprises amino acids 97 to 109 of SEQ ID NO: 1, and wherein the LCDR1 comprises amino acids 27 to 32 of SEQ ID NO: 2, the LCDR2 comprises amino acids 50 to 52 of SEQ ID NO:2, and the LCDR3 comprises amino acids 89 to 96 of SEQ ID NO: 2.

5. The isolated monoclonal antibody or antigen binding fragment of claim 1, wherein the heavy chain variable domain comprises the amino acid sequence of SEQ ID NO: 1.

6. The isolated monoclonal antibody or antigen binding fragment of claim 1, wherein the light chain variable domain comprises the amino acid sequence of SEQ ID NO: 2.

7. The isolated monoclonal antibody of claim 1, wherein the antibody is an IgG, IgM or IgA.

8. The isolated monoclonal antibody or antigen binding fragment of claim 1, wherein the monoclonal antibody or antigen binding fragment is humanized or chimeric.

9. The isolated antigen binding fragment of the isolated monoclonal antibody claim 1.

10. The isolated antigen binding fragment of claim 9, wherein the fragment is a Fab fragment, a Fab' fragment, a F(ab)'2 fragment, a single chain Fv protein (scFv), or a disulfide stabilized Fv protein (dsFv).

11. The isolated antigen binding fragment of claim 10, wherein the fragment is the scFv fragment.

12. The isolated monoclonal antibody or antigen binding fragment of claim 1, wherein the antibody or antigen binding fragment is labeled.

13. The isolated monoclonal antibody or antigen binding fragment of claim 12, wherein the label is a fluorescent, an enzymatic, heavy metal or a radioactive label.

14. A composition comprising an effective amount of the monoclonal antibody or antigen binding fragment of claim 1, and a pharmaceutically acceptable carrier.

15. An isolated nucleic acid molecule encoding the scFv fragment of claim 11.

16. The isolated nucleic acid molecule of claim 15, operably linked to a promoter.

17. An expression vector comprising the nucleic acid molecule of claim 16.

18. An isolated host cell, comprising the expression vector of claim 17.

19. A composition, comprising an effective amount of the isolated nucleic acid molecule of claim 15, an expression vector comprising the nucleic acid molecule, or a host cell comprising the expression vector, and a pharmaceutically acceptable carrier.

20. A kit for detecting the presence of emtricitabine (FTC) in a biological sample, comprising: a container comprising the isolated monoclonal antibody or antigen binding fragment of claim 1, a nucleic acid molecule encoding the isolated monoclonal antibody or antigen binding fragment, an expression vector comprising the nucleic acid molecule, or a host cell comprising the expression vector, and instructions for using the kit.

21. A method of detecting the presence of emtricitabine (FTC) in a biological sample, comprising:
   contacting a biological sample comprising emtricitabine (FTC) with an effective amount of the monoclonal antibody or antigen binding fragment that specifically binds FTC of claim 1 under conditions sufficient to form an immune complex; and
   detecting the presence of the immune complex, wherein the presence of the immune complex indicates the presence of emtricitabine (FTC) in the biological sample.

22. The method of claim 21, wherein the biological sample is a blood, serum, plasma, hair, nail, or urine sample.

23. The method of claim 21, wherein the biological sample was obtained from a subject with a human immunodeficiency virus infection (HIV), and wherein the subject has been treated with emtricitabine (FTC).

24. The method of claim 21, wherein the biological sample is obtained from a subject treated with emtricitabine (FTC) as a pre-exposure prophylaxis (PrEP).

25. The method of claim 21, wherein the biological sample is obtained from a subject treated with emtricitabine (FTC) and at least one additional anti-retroviral agent.

26. The method of claim 25, wherein the at least one additional anti-retroviral agent is tenofovir disproxil fumarate, tenofovir alfenamide, elvitegravir, or cobicistat.

27. The method of claim 21, further comprising
contacting the biological sample with a second antibody, wherein the second antibody specifically binds the monoclonal antibody or antigen binding fragment that specifically binds emtricitabine (FTC).

28. The method of claim 27, wherein the second antibody is labeled.

29. A method of determining if a subject is complying with a therapeutic or prophylactic protocol comprising emtricitabine (FTC), comprising:
contacting a solid support comprising FTC with a) a test biological sample from the subject obtained following administration of the therapeutic or prophylactic protocol to the subject and b) the monoclonal antibody or antigen binding fragment that specifically binds FTC of claim 1, under conditions sufficient to form an immune complex;
quantitating an amount of immune complex bound to the solid support, and
comparing the amount of the immune complex bound to the solid support to a control,
wherein when the amount of the immune complex bound to the solid support is the same or lower than the control the subject is complying with the therapeutic or prophylactic protocol, and when the amount of the immune complex bound to the solid support is higher than the control the subject is not complying with the therapeutic or prophylactic protocol, and
wherein the control is i) a standard value, ii) an amount of immune complex bound to the solid support comprising FTC contacted with a) a biological sample from a control subject known to be effectively treated with the therapeutic or prophylactic protocol or a biological sample comprising a known amount of FTC, and b) the monoclonal antibody or antigen binding fragment that specifically binds FTC, under the same conditions sufficient to form an immune complex.

30. The method of claim 29, wherein the monoclonal antibody or antigen binding fragment is directly labeled.

31. The method of claim 29, wherein the method further comprises contacting the solid support and the biological sample with a second monoclonal antibody that specifically binds the immune complex, wherein the second monoclonal antibody is labeled.

32. The method of claim 31, wherein the biological sample is a blood, serum, plasma, hair or urine sample.

33. The method of claim 29, wherein the biological sample was obtained from a subject with a human immunodeficiency virus infection (HIV), and wherein the subject has been treated with emtricitabine (FTC).

34. The method of claim 29, wherein the biological sample is obtained from a subject treated with emtricitabine (FTC) as a pre-exposure prophylaxis (PrEP).

35. The method of claim 29, wherein the biological sample is obtained from a subject is treated with emtricitabine (FTC) and at least one additional anti-retroviral agent.

36. The method of claim 35, wherein the at least one additional anti-retroviral agent is tenofovir disproxil fumarate, tenofovir alfenamide, elvitegravir, cobicistat, dolutegravir or bictegravir.

37. A solid support comprising the isolated monoclonal antibody of claim 1.

38. An immunoassay device comprising the solid support of claim 37.

* * * * *

SEQUENCE LISTING

```
<160> NUMBER OF SEQ ID NOS: 8

<210> SEQ ID NO 1
<211> LENGTH: 456
<212> TYPE: PRT
<213> ORGANISM: Mus musculus

<400> SEQUENCE: 1

Gln Val Gln Leu Gln Gln Pro Gly Ala Glu Leu Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Arg Ile His Leu Ser Asp Ser Asp Thr Asn Tyr Asn Gln Asn Phe
    50                  55                  60

Lys Asp Lys Ala Thr Leu Thr Val Asp Lys Ser Ser Arg Thr Ala His
65                  70                  75                  80

Met His Leu Ser Ser Leu Thr Ser Ala Asp Ser Ala Val Tyr Tyr Cys
                85                  90                  95

Ala Met Gly Gly Thr Phe Gln Ser Asn Tyr Asp Thr Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Cys Gly Asp Thr Thr Gly Ser Ser Val Thr
```

```
      130                 135                 140
Leu Gly Cys Leu Val Lys Gly Tyr Phe Pro Glu Ser Val Thr Val Thr
145                 150                 155                 160

Trp Asn Ser Gly Ser Leu Ser Ser Val His Thr Phe Pro Ala Leu
                165                 170                 175

Leu Gln Ser Gly Leu Tyr Thr Met Ser Ser Val Thr Val Pro Ser
                180                 185                 190

Ser Thr Trp Pro Ser Gln Thr Val Thr Cys Ser Val Ala His Pro Ala
                195                 200                 205

Ser Ser Thr Thr Val Asp Lys Lys Leu Glu Pro Ser Gly Pro Ile Ser
        210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
                245                 250                 255

Lys Asp Val Leu Met Ile Ser Leu Thr Pro Lys Val Thr Cys Val Val
                260                 265                 270

Val Asp Val Ser Glu Asp Asp Pro Asp Val Arg Ile Ser Trp Phe Val
                275                 280                 285

Asn Asn Val Glu Val His Thr Ala Gln Thr Gln Thr His Arg Glu Asp
        290                 295                 300

Tyr Asn Ser Thr Ile Arg Val Val Ser Ala Leu Pro Ile Gln His Gln
305                 310                 315                 320

Asp Trp Met Ser Gly Lys Glu Phe Lys Cys Lys Val Asn Asn Lys Asp
                325                 330                 335

Leu Pro Ser Pro Ile Glu Arg Thr Ile Ser Lys Ile Lys Gly Leu Val
                340                 345                 350

Arg Ala Pro Gln Val Tyr Ile Leu Pro Pro Ala Glu Gln Leu Ser
                355                 360                 365

Arg Lys Asp Val Ser Leu Thr Cys Leu Val Val Gly Phe Asn Pro Gly
        370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
                405                 410                 415

Ser Lys Leu Asp Ile Lys Thr Ser Lys Trp Glu Lys Thr Asp Ser Phe
                420                 425                 430

Ser Cys Asn Val Arg His Glu Gly Leu Lys Asn Tyr Tyr Leu Lys Lys
        435                 440                 445

Thr Ile Ser Arg Ser Pro Gly Lys
450                 455

<210> SEQ ID NO 2
<211> LENGTH: 214
<212> TYPE: PRT
<213> ORGANISM: Mus musculus

<400> SEQUENCE: 2

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
                35                  40                  45
```

Tyr Asn Ala Lys Thr Leu Thr Asp Gly Val Pro Ser Arg Phe Ser Gly
 50                  55                  60

Ser Gly Ser Gly Thr Gln Tyr Ser Leu Lys Ile Asn Ser Leu Gln Pro
 65                  70                  75                  80

Glu Asp Phe Gly Asn Tyr Tyr Cys Gln His Phe Leu Tyr Thr Pro Tyr
                 85                  90                  95

Thr Phe Gly Gly Gly Thr Lys Leu Glu Met Arg Arg Ala Asp Ala Ala
             100                 105                 110

Pro Thr Val Ser Ile Phe Pro Ser Ser Glu Gln Leu Thr Ser Gly
             115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
210

<210> SEQ ID NO 3
<211> LENGTH: 317
<212> TYPE: DNA
<213> ORGANISM: Mus musculus

<400> SEQUENCE: 3
gggcttcagt gaaggtgtcc tgcaaggcat ctggctacac cttcaccagc tactggatgc      60
actgggtgaa gcagaggcct ggccaaggcc ttgagtggat tggaaggatt catctttctg     120
atagtgatac taactacaat caaaacttca aggacaaggc cacattgact gtagacaaat     180
cctcccgcac agcccacatg catctcagca gcctgacatc tgcggactct gcggtctatt     240
attgtgcaat gggggggacc ttccagagta actacgatac ttactgggc caagggactc      300 tggtcactgt ctctgca                                                     317

<210> SEQ ID NO 4
<211> LENGTH: 381
<212> TYPE: DNA
<213> ORGANISM: Mus musculus

<400> SEQUENCE: 4
atgagtgtgc tcactcaggt cctggcgttg ctgctgctgt ggcttacagg tgccagatgt      60
gacatccaga tgactcagtc tccagcctcc ctatctgcat ctgtgggaga aactgtcacc     120
atcacatgtc gagcaagtgg gaatattcac aattatttag catggtatca gcagaaacag     180
ggaaaatctc ctcagctcct ggtctataat gcaaaaacct aacagatgg tgtgccatca      240 aggttcagtg gcagtggatc aggaacacaa tattctctca agatcaacag cctgcagcct     300
gaagattttg ggaattatta ctgtcaacat ttttgtata tccttacac gttcggaggg       360 gggaccaagc tggaaatgag a                                                381

<210> SEQ ID NO 5
<211> LENGTH: 19
<212> TYPE: PRT

```
<213> ORGANISM: Artificial Sequence
<220> FEATURE:
<223> OTHER INFORMATION: Leader

<400> SEQUENCE: 5

Met Arg Trp Ser Cys Leu Ile Leu Phe Leu Leu Ala Thr Thr Pro Gly
1               5                   10                  15

Val His Ser

<210> SEQ ID NO 6
<211> LENGTH: 120
<212> TYPE: PRT
<213> ORGANISM: Mus musculus

<400> SEQUENCE: 6

Gln Val Gln Leu Gln Gln Pro Gly Ala Glu Leu Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Arg Ile His Leu Ser Asp Ser Asp Thr Asn Tyr Asn Gln Asn Phe
    50                  55                  60

Lys Asp Lys Ala Thr Leu Thr Val Asp Lys Ser Ser Arg Thr Ala His
65                  70                  75                  80

Met His Leu Ser Ser Leu Thr Ser Ala Asp Ser Ala Val Tyr Tyr Cys
                85                  90                  95

Ala Met Gly Gly Thr Phe Gln Ser Asn Tyr Asp Thr Tyr Trp Gly Gln
            100                 105                 110

Gly Thr Leu Val Thr Val Ser Ala
        115                 120

<210> SEQ ID NO 7
<211> LENGTH: 20
<212> TYPE: PRT
<213> ORGANISM: Artificial Sequence
<220> FEATURE:
<223> OTHER INFORMATION: Leader

<400> SEQUENCE: 7

Met Ser Val Leu Thr Gln Val Leu Ala Leu Leu Leu Leu Trp Leu Thr
1               5                   10                  15

Gly Ala Arg Cys
            20

<210> SEQ ID NO 8
<211> LENGTH: 107
<212> TYPE: PRT
<213> ORGANISM: Mus musculus

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Thr Asp Gly Val Pro Ser Arg Phe Ser Gly
    50                  55                  60
```

```
Ser Gly Ser Gly Thr Gln Tyr Ser Leu Lys Ile Asn Ser Leu Gln Pro
 65                  70                  75                  80

Glu Asp Phe Gly Asn Tyr Tyr Cys Gln His Phe Leu Tyr Thr Pro Tyr
                 85                  90                  95

Thr Phe Gly Gly Gly Thr Lys Leu Glu Met Arg
                100                 105
```